United States Patent
Amano

(10) Patent No.: US 8,221,399 B2
(45) Date of Patent: Jul. 17, 2012

(54) OPHTHALMIC APPARATUS

(75) Inventor: Masanori Amano, Hazu-gun (JP)

(73) Assignee: Nidek Co., Ltd., Gamagori (JP)

( * ) Notice: Subject to any disclaimer, the term of this patent is extended or adjusted under 35 U.S.C. 154(b) by 1471 days.

(21) Appl. No.: 11/667,128

(22) PCT Filed: Dec. 1, 2005

(86) PCT No.: PCT/JP2005/022060
§ 371 (c)(1),
(2), (4) Date: May 7, 2007

(87) PCT Pub. No.: WO2006/059669
PCT Pub. Date: Jun. 8, 2006

(65) Prior Publication Data
US 2007/0299429 A1 Dec. 27, 2007

(30) Foreign Application Priority Data
Dec. 1, 2004 (JP) .................... 2004-349034

(51) Int. Cl.
*A61B 18/20* (2006.01)
*G05B 21/00* (2006.01)

(52) U.S. Cl. ............... 606/4; 606/10; 359/368; 351/208; 351/210

(58) Field of Classification Search .......... 351/205–212; 606/4–6, 10–17; 359/368–394; 250/311
See application file for complete search history.

(56) References Cited

U.S. PATENT DOCUMENTS

| | | | | |
|---|---|---|---|---|
| 4,911,543 A * | 3/1990 | Hodgson | ....................... | 359/369 |
| 5,271,592 A * | 12/1993 | Ludwig | ....................... | 248/333 |
| 5,351,925 A * | 10/1994 | Druais | ....................... | 248/325 |
| 5,719,388 A | 2/1998 | Tokunaga | | |
| 5,825,536 A * | 10/1998 | Yasunaga et al. | ............. | 359/384 |
| 6,018,415 A * | 1/2000 | Woo et al. | ....................... | 359/393 |
| 6,159,202 A | 12/2000 | Sumiya et al. | | |
| 6,579,282 B2 | 6/2003 | Bille et al. | | |
| 6,592,086 B1 | 7/2003 | Sander | | |
| 7,118,561 B2 | 10/2006 | Suguira | | |
| 2003/0144651 A1 | 7/2003 | Teiwes et al. | | |
| 2004/0143246 A1 | 7/2004 | Maeda et al. | | |
| 2004/0184143 A1* | 9/2004 | Akiyama et al. | ............. | 359/381 |

FOREIGN PATENT DOCUMENTS

| | | |
|---|---|---|
| JP | A 5-269145 | 10/1993 |
| JP | A 6-254053 | 9/1994 |
| JP | A 9-149914 | 6/1997 |

(Continued)

*Primary Examiner* — Ahmed Farah
(74) *Attorney, Agent, or Firm* — Oliff & Berridge, PLC

(57) ABSTRACT

To irradiate a laser beam appropriately onto a patient's eye. An ophthalmic apparatus having a laser irradiation optical system irradiating a laser beam for corneal surgery onto the eye, which performs alignment of a reference axis of the optical system to have a predetermined positional relationship with the eye to perform laser irradiation, includes movement means changing inclination and a position of the optical system with respect to the eye, first and second image-pickup means picking up anterior-segment images having image-pickup optical axes arranged in different directions and to have predetermined positional relationships with the reference axis, detection means for detecting inclination and a position of the eye with respect to the reference axis by subjecting the images by the image-pickup means to image processing, and control means controlling the movement means to bring the reference axis to an intended alignment state with the eye based on a detection result.

12 Claims, 15 Drawing Sheets

FOREIGN PATENT DOCUMENTS

| | | |
|---|---|---|
| JP | B2 3096474 | 8/2000 |
| JP | A 2002-330989 | 11/2002 |
| JP | A 2003-111776 | 4/2003 |
| JP | A 2003-534050 | 11/2003 |
| JP | A 2004-89215 | 3/2004 |
| JP | A 2004-215889 | 8/2004 |

* cited by examiner

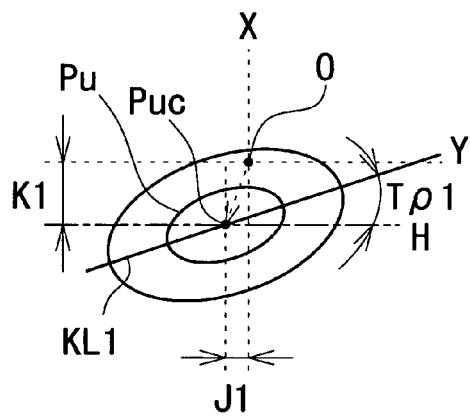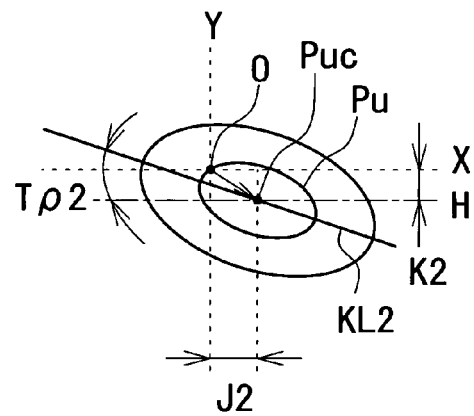
FIG. 17A  FIG. 17B
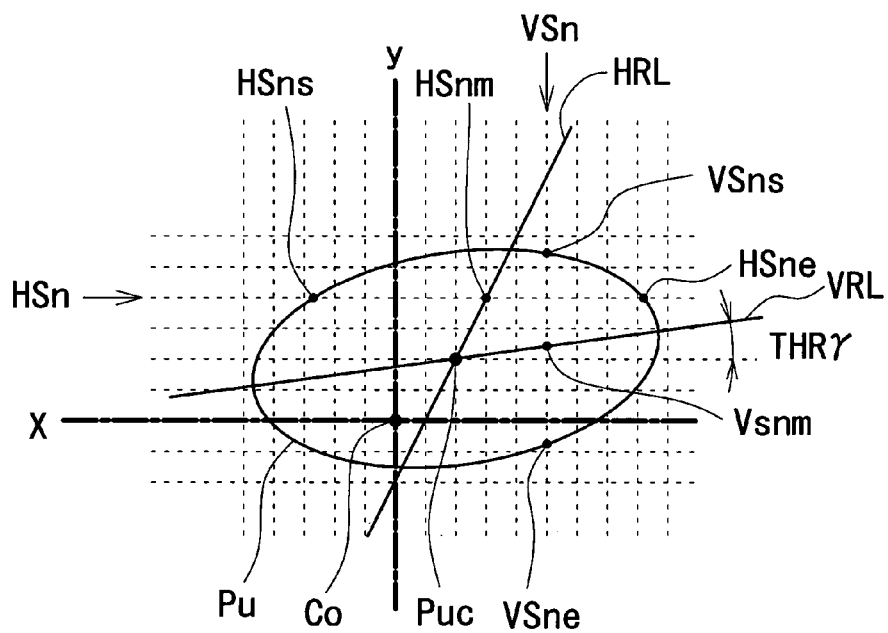
FIG. 18

OPHTHALMIC APPARATUS

TECHNICAL FIELD

The present invention relates to an ophthalmic apparatus having a microscope for observing an eye and an ophthalmic apparatus which performs laser irradiation onto a patient's eye.

BACKGROUND ART

Conventionally, a surgical microscope in which a microscope for observing an eye can be directed toward an arbitrary position and direction three-dimensionally, has a configuration including axes dedicated for movement and direction change (e.g., Japanese Patent Application Unexamined Publication No. 2003-111776).

In addition, in an ophthalmic apparatus incorporating a laser irradiation optical system for ablating a cornea for refractive surgery, a laser irradiation end is provided beneath a microscope since it is necessary to perform laser irradiation while observing an eye (e.g., Japanese Patent Application Unexamined Publication No. Hei09-149914). In order to move the laser irradiation end, this apparatus has a slide arm movable horizontally, and an arm tip portion movable vertically on which the microscope is placed. In the apparatus, the microscope and the laser irradiation end have degrees of flexibility in three-axis directions of horizontal directions and a vertical direction.

DISCLOSURE OF THE INVENTION

Problem to be Solved by the Invention

However, the conventional ophthalmic apparatuses have problems as follows. In such an apparatus incorporating the laser irradiation optical system disclosed in Japanese Patent Application Unexamined Publication No. Hei09-149914, the directions of the microscope and the laser irradiation optical system cannot be changed in accordance with an inclination direction of an eye, so that there is a problem that it is difficult to perform laser irradiation with reference to a fixed position on a cornea. In addition, even if a position of a patient's face is corrected first and then a position for observation or conditions for surgery are determined in preparation for surgery, it is often the case that the patient fails to keep the face position and moves the face during surgery. If the face is inclined; the eye is also inclined. If the eye moves during surgery, it is necessary to take steps to suspend the surgery to move the microscope, to move the patient's face again or the like, which prevents smooth surgery. In addition, it is often the case that the patient fails to fix a line of sight to cause eye rotation.

It is difficult for a mechanism such that the microscope is fixed in line by every one axis as disclosed in Japanese Patent Application Unexamined Publication No. 2003-111776 to ensure stiffness in order to always capture an affected part necessary for observation as a target to make the microscope and the laser irradiation end track the target by remote control. In addition, it is necessary to arrange driving sources for moving and controlling the microscope on the axes by remote control in the vicinities of the respective axes, and if the number of the axes increases, the mechanism becomes more complex to cause an increase in weight. Therefore, there is a problem that positioning of the microscope and the laser irradiation end is difficult.

The present invention has been made in view of the above circumstances and has an object to overcome the above problems and to provide an ophthalmic apparatus capable of properly irradiating a laser beam onto a patient's eye, and to provide an ophthalmic apparatus capable of performing easy positioning of a microscope in order to appropriately observe a patient's eye.

Means for Solving the Problems

To solve the above problems, the present invention is characterized as having configurations described below.

(1) An ophthalmic apparatus having a laser irradiation optical system for irradiating a laser beam for corneal surgery onto a patient's eye, which performs alignment of a reference axis of the laser irradiation optical system so that the reference axis has a predetermined positional relationship with the patient's eye to perform irradiation of the laser beam, is characterized as including movement means for changing inclination and a position of the laser irradiation optical system with respect to the patient's eye, first image-pickup means and second image-pickup means for picking up images of an anterior segment of the patient's eye which have image-pickup optical axes arranged in different directions and arranged to have respective predetermined positional relationships with the reference axis, detection means for detecting inclination and a position of the patient's eye with respect to the reference axis by subjecting the anterior-segment images picked up by the first and second image-pickup means to image processing, and control means for controlling the movement means so that the reference axis is brought to an intended alignment state with respect to the patient's eye based on a result of detection by the detection means.

(2) The ophthalmic apparatus according to (1) is characterized that the detection means obtains pupil shapes by subjecting the anterior-segment images picked up by the first and second image-pickup means to the image processing, and detects the inclination of the patient's eye based on distortion of the obtained pupil shapes with respect to pupil shapes in the intended alignment state.

(3) The ophthalmic apparatus according to (2) is characterized that the detection means detects the inclination of the patient's eye based on size ratios of the pupil shapes in at least two directions with reference to pupil centers of the pupil shapes.

(4) The ophthalmic apparatus according to (2) is characterized that the image-pickup optical axes of the first and second image-pickup means are arranged inclined in different directions with respect to the reference axis, and the detection means detects the inclination of the patient's eye based on distortion directions of the obtained pupil shapes.

(5) The ophthalmic apparatus according to (4) is characterized that, as for the obtained pupil shapes, the detection means obtains the distortion directions based on middle positions of pupil edges which are obtained by scanning the obtained pupil shapes horizontally and vertically respectively on a plurality of lines.

(6) The ophthalmic apparatus according to (1) is characterized that the control means controls the movement means based on changes in inclination and a position of the patient's eye obtained by the detection means at the time of the irradiation with respect to inclination and a position of the patient's eye obtained by the detection means in the intended alignment state.

(7) The ophthalmic apparatus according to (1) is characterized that the movement means has a parallel-link mechanism including at least six control rods which support the laser irradiation optical system while supporting positions thereof can be changed individually; and driving sources which drive the control rods respectively.

(8) An ophthalmic apparatus having a laser irradiation optical system for irradiating a laser beam for corneal surgery onto a patient's eye, which performs alignment of a reference axis of the laser irradiation optical system so that the reference axis has a predetermined positional relationship with the patient's eye to perform irradiation of the laser beam, is characterized as including movement means for changing inclination and a position of the laser irradiation optical system with respect to the patient's eye, first image-pickup means and second image-pickup means for picking up images of an anterior segment of the patient's eye which have image-pickup optical axes arranged in different directions and arranged to have respective predetermined positional relationships with the reference axis, detection means for detecting inclination and a position of the patient's eye with respect to the reference axis by subjecting the anterior-segment images picked up by the first and second image-pickup means to image processing, and display means for displaying information on the inclination and the position of the patient's eye detected by the detection means.

(9) An ophthalmic apparatus is characterized as including a microscope for observing a patient's eye, a parallel-link mechanism which changes inclination and a position of the microscope including at least six control rods which support a movement part in which the microscope is installed and driving sources which drive the control rods respectively, input means for inputting signals for changing the inclination and the position of the microscope, and control means for controlling an operation of the parallel-link mechanism based on the input signals.

(10) The ophthalmic apparatus according to (9) is characterized that the at least six control rods included in the parallel-link mechanism are control rods capable of changing bending angles or capable of expanding and contracting.

(11) The ophthalmic apparatus according to (9) is characterized that, when the signal for changing the inclination is inputted by the input means, the control means controls the operation of the parallel-link mechanism to incline the microscope taking a predetermined position on an optical axis of an objective lens included in the microscope as a reference position, and controls the operation of the parallel-link mechanism to keep a distance between the reference position and the objective lens.

(12) The ophthalmic apparatus according to (9) is characterized as further including detection means having image-pickup means installed in the movement part in order to pick up an image of the patient's eye, for detecting an alignment state including inclination of the eye by subjecting the eye image picked up by the image-pickup means to image processing, and is characterized that the control means controls the operation of the parallel-link mechanism so that the microscope has a predetermined positional relationship with the patient's eye based on a result of detection by the detection means.

(13) The ophthalmic apparatus according to (12) is characterized that the control means controls the operation of the parallel-link mechanism so that the inclination and the position of the microscope track movement of the patient's eye based on the detection result by the detection means.

(14) The ophthalmic apparatus according to (9) is characterized as further including first image-pickup means and second image-pickup means for picking up images of an anterior segment of the patient's eye, which have image-pickup optical axes arranged in different directions and arranged to have respective predetermined positional relationships with a reference axis of the microscope, and detection means for detecting inclination and a position of the patient's eye with respect to the reference axis by subjecting the anterior segment images picked up by the first and second image-pickup means to image processing, wherein the control means controls the operation of the parallel-link mechanism so that the microscope is brought to an intended alignment state with respect to the patient's eye based on a result of detection by the detection means.

Effect of the Invention

According to the present invention, it is possible to appropriately irradiate a laser beam onto a patient's eye. In addition, it is possible to perform easy positioning of a microscope in order to appropriately observe a patient's eye.

BRIEF DESCRIPTION OF THE DRAWINGS

FIGS. 17A and 17B are views for illustrating inclination of elliptical shapes of the pupil edge picked up by the two cameras when the eye is inclined in the X-axis and Y-axis directions and the eye has positional deviations in the X- and Y-directions;

FIG. 18 is a view for illustrating a simplified method of detecting information on the positions and the eye inclination;

BEST MODE FOR CARRYING OUT THE INVENTION

Figure 1:
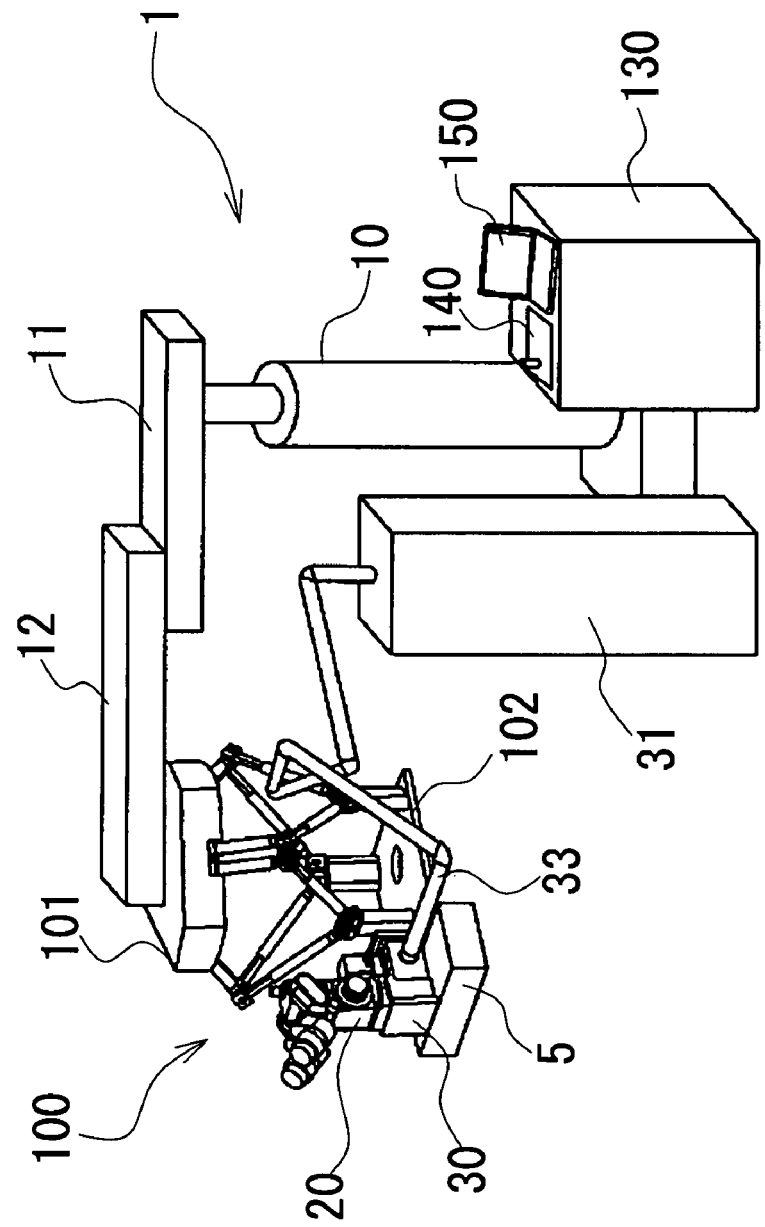
FIG. 1 is a view showing a schematic configuration of a whole ophthalmic apparatus having a surgical microscope and a laser irradiation unit.

A detailed description of one preferred embodiment of the present invention is provided below with reference to the accompanying drawings. FIG. 1 is a view showing a schematic configuration of a whole ophthalmic apparatus having a surgical microscope and a laser irradiation unit.

In FIG. 1, a surgical microscope 1 has a first horizontal joint arm 11 and a second horizontal joint arm 12 which are provided on a pole leg 10, the second horizontal joint arm 12 holding a fixation part 101 of a parallel-link mechanism 100. In this embodiment, two horizontal joint arms are employed in order to roughly move the parallel-link mechanism 100; however, a vertical joint arm or a combined type thereof may be employed. The parallel-link mechanism 100 supports a movement part 102 to be movable with respect to the fixation part 101 by six control rods 111 to 116 (see FIG. 2). In the movement part 102, a microscope 20 and a laser irradiation end unit 30 are installed. Positions and inclination of the microscope 20 and the unit 30 provided in the movement part 102 can be arbitrarily changed by the parallel-link mechanism 100. A control rod 130 is for controlling the parallel-link mechanism 100 and the like. An operation panel 140 for remote control is for inputting an operation signal for operating the parallel-link mechanism 100.

In addition, in this ophthalmic apparatus, the laser irradiation end unit 30 is placed beneath the microscope 20, and a therapeutic laser beam for corneal ablation (e.g., an excimer laser beam) is guided from a main body 31 of a laser irradiation apparatus to the laser irradiation end unit 30 via a multi-joint arm 33. Mirrors for reflecting the therapeutic laser beam are arranged at joint parts of the multi-joint arm 33. An end portion of the multi-joint arm 33 is capable of tracking arbitrary movement. For guiding the laser beam from the main body 31 of the laser irradiation apparatus to the laser irradiation end unit 30, it is enough to employ a light guide capable of tracking arbitrary movement of the movement part 102, and an optical fiber may be employed. An illumination unit 5 is arranged beneath the laser irradiation end unit 30.

Figure 2:
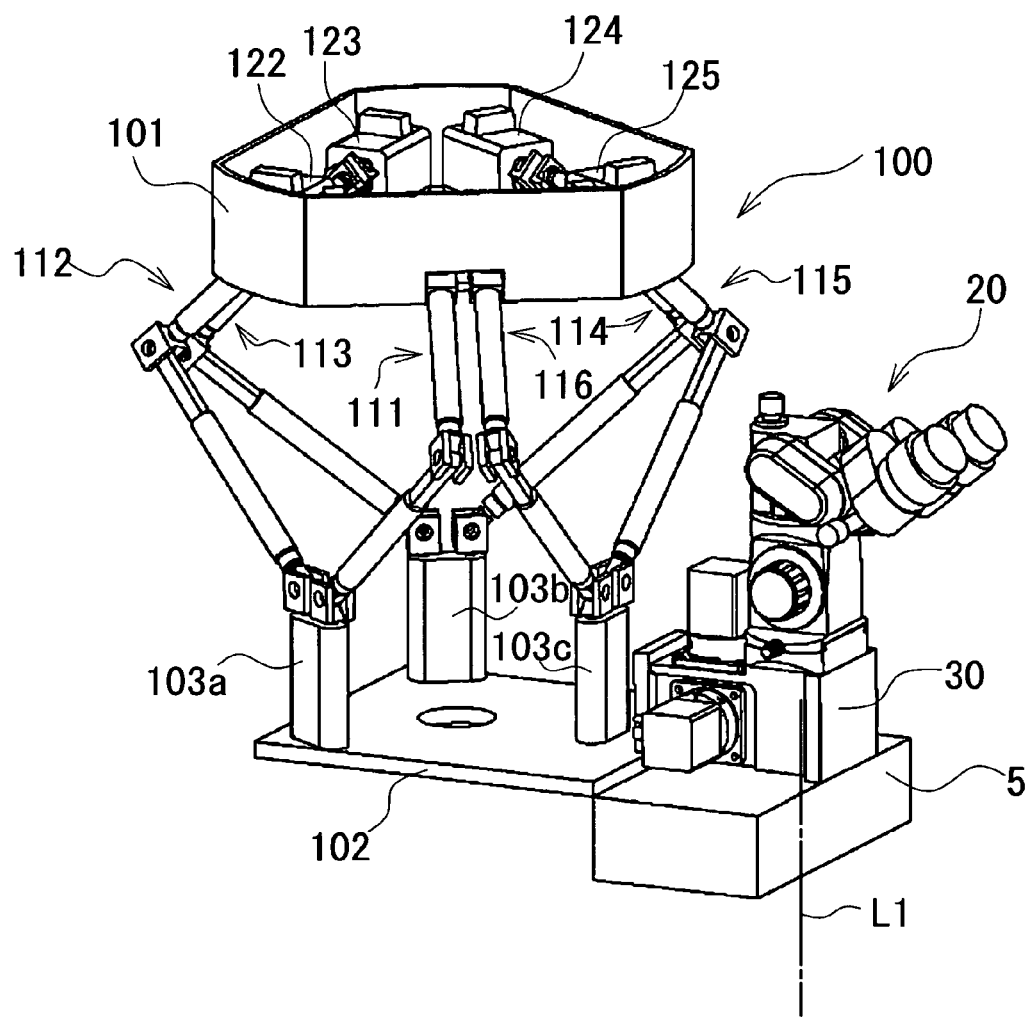
FIG. 2 is a view for illustrating a configuration of a parallel-link mechanism.

Next, a configuration of the parallel-link mechanism 100 is described with reference to FIG. 2 and FIG. 3. FIG. 2 is a perspective view showing a state of arrangement of the whole parallel-link mechanism 100, the microscope 20 and the like. In FIG. 2, the parallel-link mechanism 100 has the six control rods 111, 112, 113, 114, 115 and 116 for changing a position and inclination of the movement part 102 with respect to the fixation part 101. Motors 121 to 126 being driving sources for respectively driving the control rods 111 to 116 respectively are arranged in the fixation part 101 (in FIG. 2, the motors 121 and 126 are not illustrated).

Figure 3:
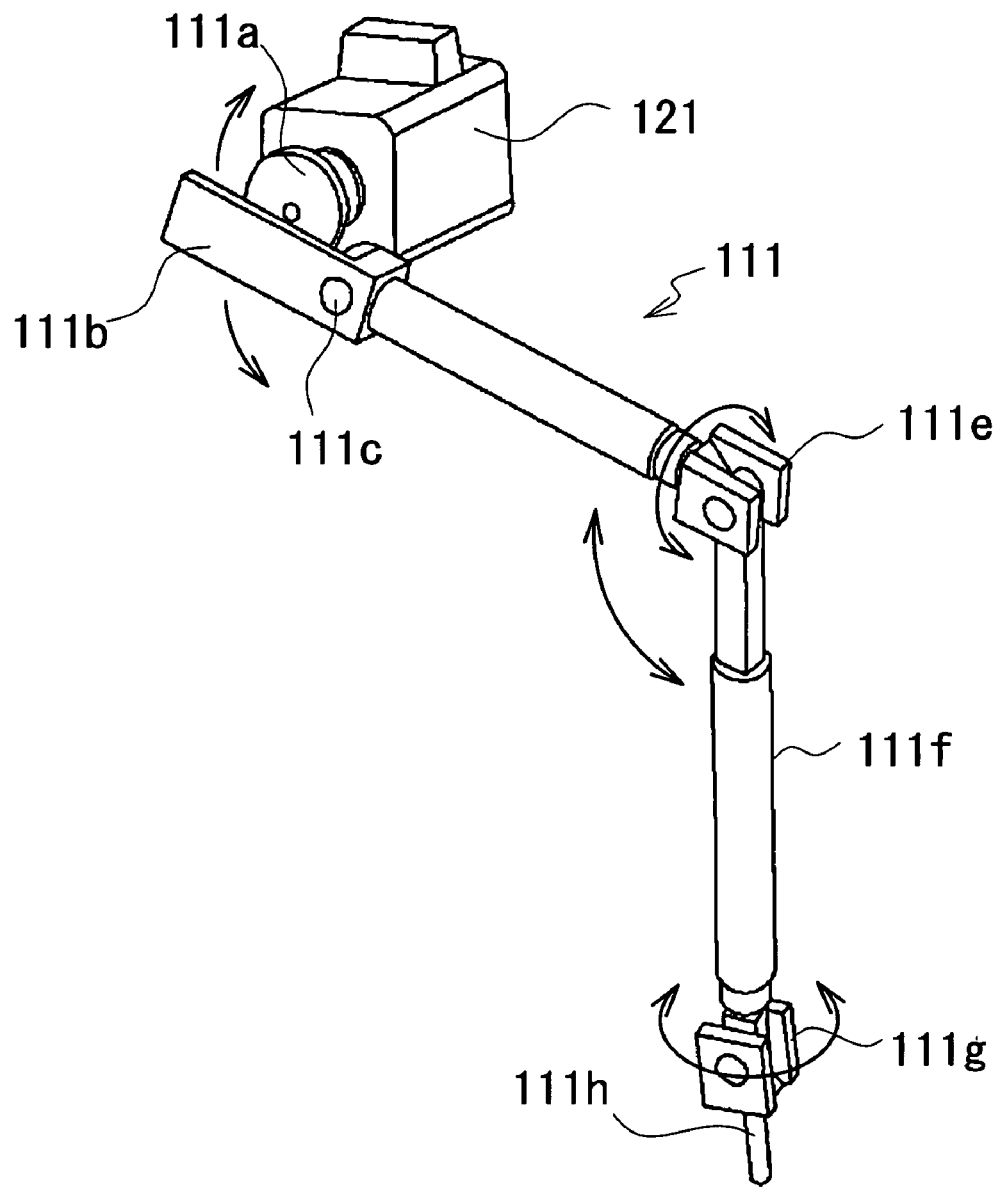
FIG. 3 is a view for illustrating a configuration of a control rod in the parallel-link mechanism.

FIG. 3 is a view for illustrating a configuration of the one control rod 111. An eccentric cam 111a is mounted to a rotation axis of the motor 121. Rotation of the eccentric cam 111a makes a base part 111b of the control rod 111 rotatable on a vertical plane about a center axis 111c held by the fixation part 101. A first driving axis 111d is attached to the base part 111b, and a first bearing 111e rotatable about the axis is attached to an end of the first driving axis 111d. A second driving axis 111f is attached to the first bearing 111e so that a bending angle can be changed with respect to the first driving axis 111d. Further, a second bearing 111g is attached to an end of the second driving axis 111f, which is rotatable about the axis. An axis 111h is attached to the second bearing 111g so that an angle can be changed with respect to the second driving axis 111f. The axis 111h is attached to a supporting block 103a fixed to the movement part 102.

The other control rods 112 to 116 have the same configuration as the control rod 111. The control rod 112 is attached to the supporting block 103a, the control rods 113 and 114 are attached to a supporting block 103b, and the control rods 115 and 116 are attached to a supporting block 103c. By simultaneously controlling the motors 121 to 126 provided in the fixation part 101 which respectively correspond to the control rods 111 to 116 respectively, a position and inclination of the microscope 20 installed in the movement part 102 are made changeable arbitrarily. Besides, the microscope 20 is attached to the movement part 102 via the laser irradiation end unit 30.

Figure 4:
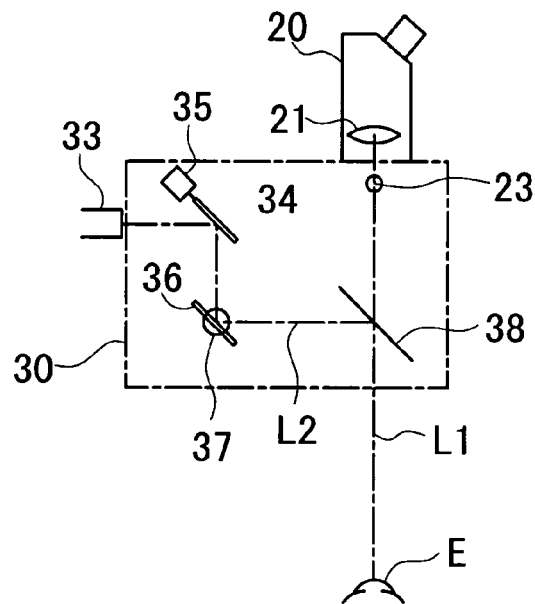
FIG. 4 is a view showing a schematic configuration of an optical system installed in a laser irradiation end unit.

FIG. 4 is a view showing a schematic configuration of a laser irradiation optical system installed in the laser irradiation end unit 30. The laser beam outputted from the multi-joint arm 33 is scanned two-dimensionally by a first galvano mirror 34 and a second galvano mirror 36 being scanning mirrors. Between an objective lens 21 of the microscope 20 and a patient's eye E, a dichroic mirror 38 which reflects the laser beam for corneal ablation and transmits visible observation light is arranged. The dichroic mirror 38 makes a reference optical axis L2 of the irradiation optical system coaxial with an optical axis L1 of the objective lens 21. In addition, a fixation light 23 is arranged on the optical axis L1 of the objective lens 21, and the patient eye E is made to fixate the fixation light 23 during surgery.

The laser beam with a small-diameter spot exiting from the multi-joint arm 33 is scanned two-dimensionally on a cornea of the patient's eye E by the galvano mirrors 34 and 36. A spot diameter of the laser beam to be irradiated onto the cornea is preferably the order of 0.1 to 1 mm. A laser beam is a beam in which energy density decreases gradually from the center to its periphery. The cornea can be ablated into an arbitrary shape by scanning the small-spot laser beam two-dimensionally on the cornea and overlapping the laser beam. In refractive surgery, corneal curvature is changed by overlapping the small-spot laser beam.

Figure 5:
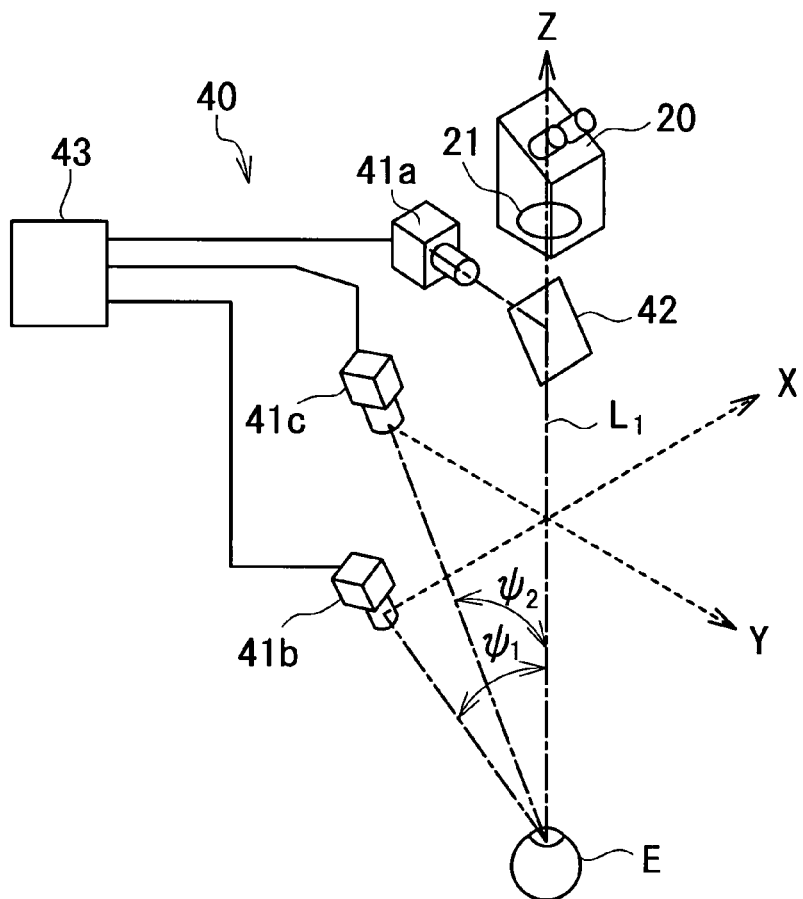
FIG. 5 is a view for illustrating a configuration of a mechanism for eye detection.

In addition, the surgical microscope 1 is provided with a mechanism 40 for eye detection which detects an alignment state of the patient's eye including inclination of the eye. The mechanism 40 for eye detection also detects movement of the eye. As shown in FIG. 5, the mechanism 40 for eye detection has three image-pickup cameras 41a, 41b and 41c as image-pickup means for picking up images of an anterior segment of the patient's eye. The cameras 41a to 41c are installed in the movement part 102 to move integrally with the microscope 20. The camera 41a is arranged in a position where the anterior-segment image of the patient's eye E is picked up from a direction of the optical axis L1 of the microscope 20 via a light-dividing member 42 such as a half mirror arranged on the optical axis L1. The cameras 41b and 41c are arranged in positions where the anterior-segment images of the patient's eye E are picked up from directions where respective image-pickup optical axes of the cameras become oblique to the optical axis L1, having positional relationships such that an X-axis direction and a Y-axis direction which are orthogonal to the optical axis L1 intersect at right angle. In addition, the cameras 41a to 41c are arranged so that the cameras attain focus at a focal point of the objective lens 21 on the optical axis L1. Image-pickup signals from the cameras 41a to 41c are inputted to an image processing part 43. Sampling frequencies of the cameras 41a to 41c are preferably 200 Hz or more. The image processing part 43 detects positional deviations of the patient's eye E on a plane orthogonal to the optical axis L1 (X-Y positions), a distance of the patient's eye E to the objective lens 21 (a Z position), and inclination of the patient's eye E with respect to the optical axis L1 (an angle and a direction of the inclination).

Figure 6:
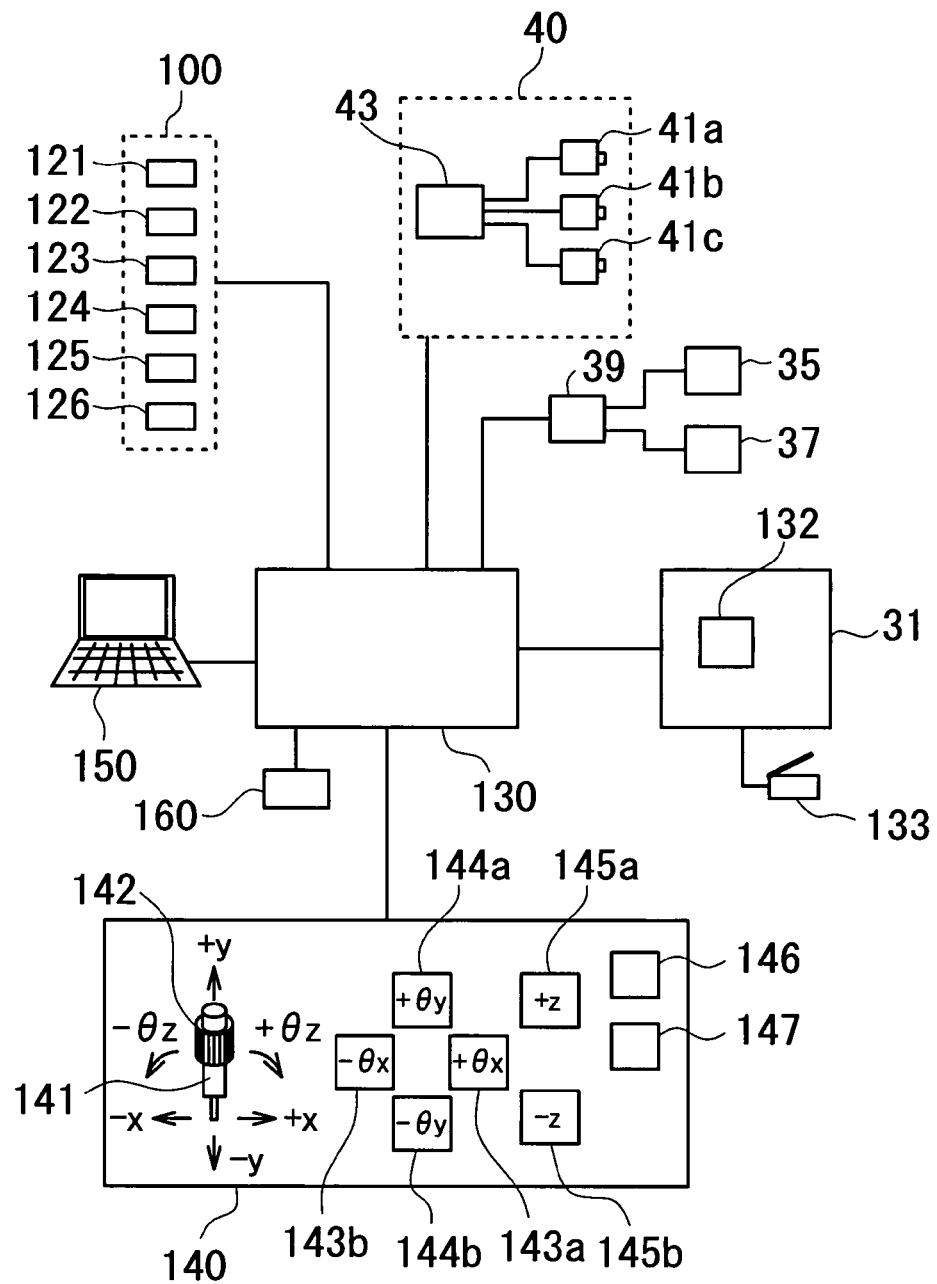
FIG. 6 is a block diagram of a control system of the ophthalmic apparatus.

FIG. 6 is a block diagram of a control system of the ophthalmic apparatus. The control unit 130 is connected with the operation panel 140, which is signal input means for inputting an operation signal and the like to operate the parallel-link mechanism 100 to change a position and attitude of a microscope 3 together with the movement part 102, the image processing part 43, a scanning control part 39 which controls driving parts 35 and 37 of the galvano mirrors, the main body 31 of the laser irradiation apparatus, a data input device 150, and the like. An ultraviolet laser source 132 which emits the laser beam capable of corneal ablation is arranged inside the main body 31 of the laser irradiation apparatus.

In the operation panel 140, arranged are a lever 141 for inputting a signal to move the microscope 20 placed in the movement part 102 in a horizontal direction (X- and Y-directions), a rotation knob 142 for inputting a signal to rotate the microscope 20 about a predetermined axis, switches 143a and 143b for inputting a signal to incline the microscope 20 in the X-direction (a signal to change an inclination angle of the microscope 20), switches 144a and 144b for inputting a signal to incline the microscope 20 in the Y-direction (a signal to change the inclination angle of the microscope 20), and switches 145a and 145b for inputting a signal to move the microscope 20 up and down. In addition, a switch 146 is a for starting automatic alignment, and a switch 147 is for starting automatic tracking after the microscope 20 is placed to have an intended positional relationship with the patient's eye.

Next, in the apparatus having the above-mentioned configuration, described are alignment of the microscope 20 and an operation of laser irradiation by the parallel-link mechanism 100.

The patient undergoes surgery in a state where he/she is lying on his/her back on an unillustrated bed. An operator manually moves the first horizontal joint arm 11 and the second horizontal joint arm 12 of the surgical microscope 1 to place the microscope 20 roughly above the patient's eye to be operated on (patient's eye E). The patient's eye E is fixated on the fixation light 23 to guide a visual line to a direction of the fixation light 23. Precise alignment with the patient's eye E can be performed by operating the switches in the operation panel 140 to operate the parallel-link mechanism 100 while the patient's eye E is observed under the microscope 20. The control unit 130 controls the motors 121 to 126 simultaneously under operation signals from the switches to change the positions and the inclination of the microscope 20 and the laser irradiation end unit 30 placed in the movement part 102.

Figure 7A:
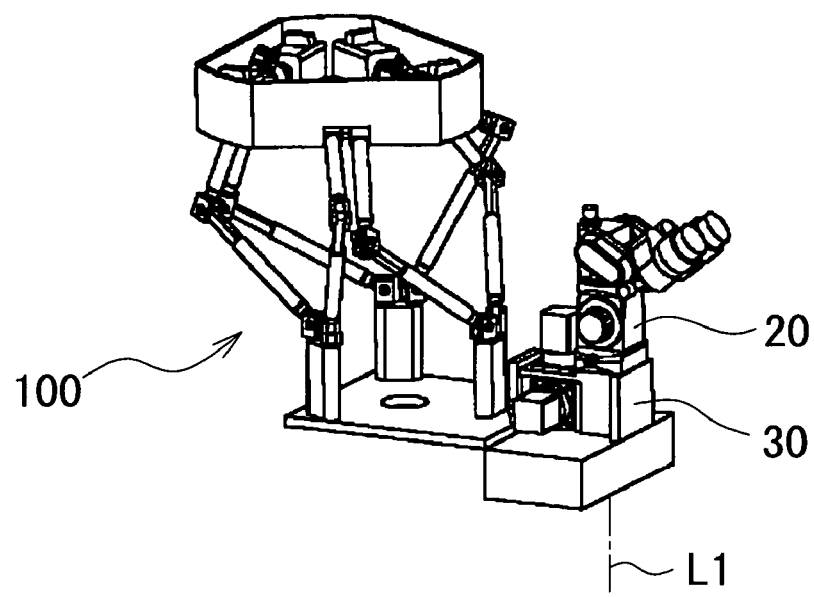
FIGS. 7A and 7B are views for showing a state of change in positions and inclination of the microscope by the parallel-link mechanism.
Figure 7B:
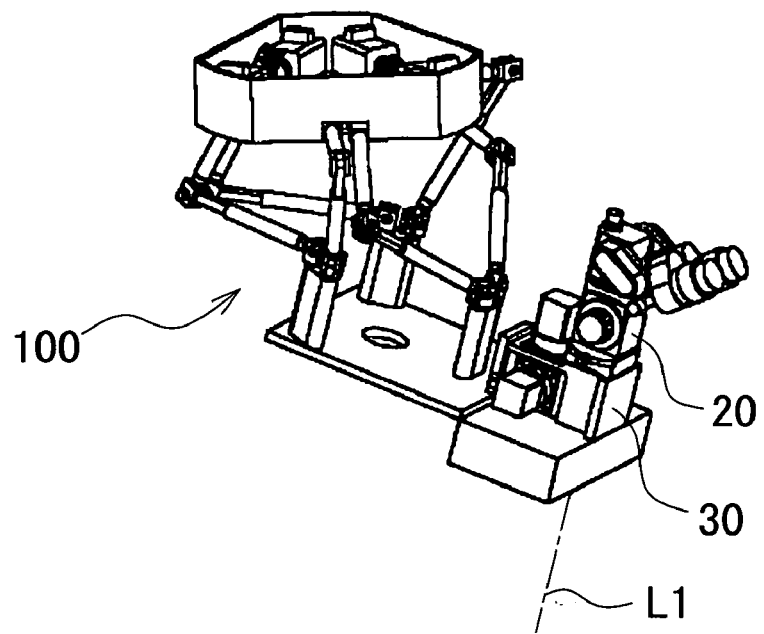

For example, in a state as shown in FIG. 2, simultaneously increasing/decreasing bending amounts of the six control rods 111 to 116 allows the position of the microscope 20 to go up/down. In addition, as shown in FIG. 7A, changing the bending amounts of the control rods 111 and 114 while decreasing the bending amounts of the control rods 115 and 116 and increasing the bending amounts of the control rods 112 and 113 allows the microscope 20 to move rightward in FIG. 7A (toward the front of an examiner). Further, as shown in FIG. 7B, changing the bending amounts of the control rods 111 to 116 allows the microscope 20 to be inclined.

Figure 8:
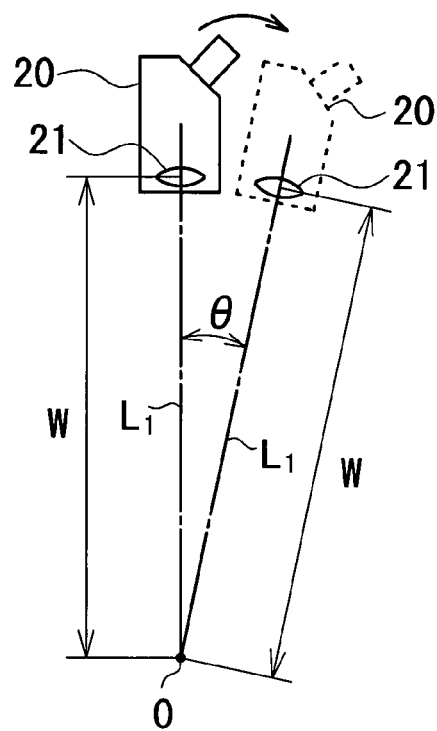
FIG. 8 is a view for illustrating movement in changing an inclination angle of a microscope 20 while maintaining an observed position under the microscope 20.

Here, at the time of changing the inclination angle of the microscope 20, the control unit 130 controls the operation of the parallel-link mechanism 100 so as to change only an angle of an observation direction while maintaining the observed position under the microscope 20. As shown in FIG. 8, on the optical axis L1 of the objective lens 21 included in the microscope 20, assume that a position at a distance of W from the objective lens 21 is a reference point O to be observed. If signals for changing the inclination angle are inputted with the switches 143a, 143b, 144a and 144b, the control unit 130 controls the operation of the parallel-link mechanism 100 to incline the microscope 20 at an angle $\theta$ of an inclination change with fixing the reference point O while changing a horizontal position and a vertical position of the microscope 20 with keeping the distance W between the reference point O and the objective lens 21. In other words, the microscope 20 is moved on an arc line at the angle $\theta$ of the inclination change with reference to the reference point O. Accordingly, the switch operation for changing the inclination angle can change only the observation direction without changing the observed position of the patient's eye under the microscope 20, which is convenient. Besides, the distance W is set as a focal distance of the objective lens 21; however, the distance W may be set as a predetermined distance by setting the data input device 150 having a monitor.

In addition, the microscope 20 can be rotated having a predetermined vertical reference axis as its center. The vertical reference axis can be set coaxial with the optical axis L1 of the objective lens 21 in the microscope 20 in a state as shown in FIG. 2, or can be changed arbitrarily.

Thus, by changing the respective bending amounts of the six control rods 111 to 116, six types of degrees of flexibility in a right-and-left direction (X), a back-and-forth direction (Y), an up-and-down direction (Z), a back-and-forth inclination angle ($\theta y$), a right-and-left inclination angle ($\theta x$), and a rotation ($\theta z$) are provided. Accordingly, the position and attitude of the microscope 20 with respect to the patient's eye E can be determined appropriately. As for the positioning, since the movement part 102 in which the microscope 20 is placed is supported by the six control rods 111 to 116 being support axes, precise positioning with complete control can be achieved while possessing high stiffness in spite of the simple configuration.

In addition, after the determination of the position and the attitude of the microscope 20, the mechanism 40 for eye detection is actuated by pressing the switch 147 to establish automatic tracking mode. The anterior-segment images of the patient's eye E picked up by the cameras 41a, 41b and 41c are inputted to the image processing part 43. Triggered by a signal from the switch 147, the control unit 130 sets a position of the anterior-segment images picked up at this point as a reference state (an intended state). The position of the patient's eye E can be detected, for example, by subjecting a pupil edges or pupil centers in the anterior-segment images to image processing. When the patient's eye E moves in the right-and-left and back-and-forth directions (X- and Y-directions), a pupil, images of which are to be picked up by the cameras 41a to 41c, moves. If the patient's eye E moves in the up-and-down direction (Z-direction), a position of the pupil, images of which are to be picked up by the cameras 41b and 41c, changes. The control unit 130 drives and controls the parallel-link mechanism 100 to move the position of the microscope 20 in accordance with the movement of the patient's eye E so as to bring the anterior-segment images picked up by the cameras 41a to 41c to the reference state.

Figure 9:
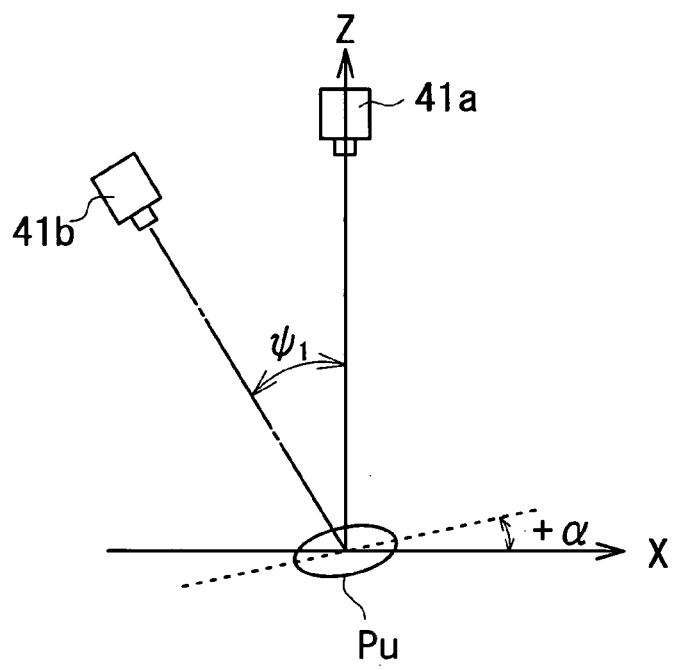
FIG. 9 is a view for illustrating detection of an inclination state of a patient's eye.

An inclination state of the patient's eye E can be detected based on the images obtained by the cameras 41b and 41c arranged in the X- and Y-directions. For example, as shown in FIG. 9, assume that a pupil edge Pu which are circular in the reference state is inclined at an angle +α in the X-direction. The pupil edge Pu image to be picked up by the first camera 41a alters its shape from the circular shape to an elliptical shape inclined at the angle α in the X-direction. Meanwhile, the pupil edge Pu image to be picked up by the second camera 41b placed inclined at an angle ψ1 in the X-axis direction with respect to the first camera 41a alter its shape to a shape inclined at an angle (ψ1−α) with respect to an elliptical shape at the angle ψ1. Based on these, an inclination angle and an inclination direction (+ direction or − direction) in the X-direction are detected. Similarly, by the third camera 41c placed inclined at an angle ψ2 in the Y-direction with respect to the first camera 41a, an inclination angle and an inclination direction (+ direction or − direction) in the Y-direction are detected. The control unit 130 drives and controls the parallel-link mechanism 100 based on feedback on the detected information to change the inclination angle of the microscope 20 and change the horizontal position and the vertical position of the microscope 20 so as to bring a positional relationship between the patient's eye and the microscope 20 to the initial reference state. Accordingly, the operator can observe the patient's eye E in a proper state in accordance with the movement of the eye including the eye inclination in addition to the positional changes in the X-, Y- and Z-directions.

Further, rotation of the patient's eye E about a visual axis can be detected by processing a characteristic point such as an iris pattern in the anterior-segment image picked up by the camera 41a. By changing rotation of the microscope 20 based on thus-detected information, the patient's eye E can be observed more appropriately.

In the above, the positioning for the initial reference state is performed through the operation of the operation panel 140 by the operator; however, it can be performed also by automatic alignment so as to be brought to a predetermined reference state. The reference state for the alignment is determined as, for example, a state where the optical axis L1 is made to coincide with the pupil center and the optical axis L1 is vertical to an iris surface. After setting the automatic alignment by pressing the switch 146, when the patient's eye E falls within a detectable area of the cameras 41a to 41c by roughly aligning the microscope 20 with the patient's eye E, the automatic alignment is activated. Based on information detected by the three cameras 41a to 41c, the control unit 130 drives and controls the parallel-link mechanism 100 so that an observation state of the microscope 20 is brought to the reference state.

When the position of the microscope 20 is brought to an appropriate state, the therapeutic laser beam is made ready for irradiation. When the operator depresses a footswitch 133 to input a trigger signal for laser irradiation, the ultraviolet laser source 132 arranged inside the main body 31 of the laser irradiation apparatus is driven. The laser beam from the main body 31 of the laser irradiation apparatus is guided to the laser irradiation end unit 30 by the multi-joint arm 33. The control part 39 for the galvano mirrors drives and controls the galvano mirrors 34 and 36 according to corneal correction data inputted by the data input device 150 in advance. By driving the galvano mirrors 34 and 36, the laser beam with the small diameter spot reflected by the dichroic mirror 38 is scanned on the cornea of the patient's eye E to be overlapped, ablating the cornea into an intended shape.

Also at the time of the laser irradiation, when the patient's eye E moves, the parallel-link mechanism 100 is driven based on detected information by the mechanism 40 for eye detection to move the laser irradiation end unit 30 together with the microscope 20 in accordance with the movement of the patient's eye. Accordingly, the laser beam is irradiated onto a proper position on the cornea in accordance with the movement of the patient's eye including the eye inclination.

Figure 10A:
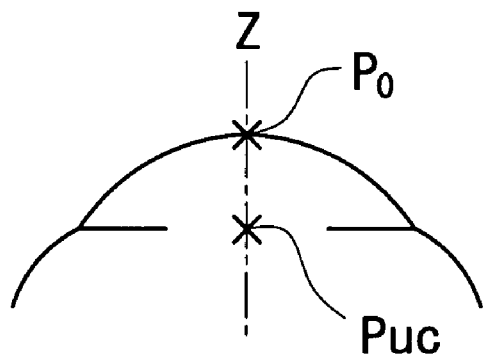
FIGS. 10A and 10B are views for illustrating movement for irradiating a laser beam onto a proper position on a cornea in accordance with the inclination of the patient's eye.
Figure 10B:
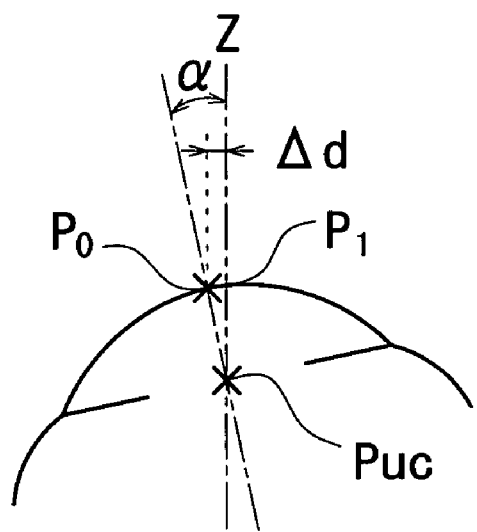

For example, assume that the patient's eye E is inclined at an angle α as shown in FIG. 10B from a state where the eye is in the horizontal direction as shown in FIG. 10A, because of attitude change of the face or eye rotation (duction of the eye). Assume that the laser beam is irradiated with reference to a pupil center Puc. In a state as shown in FIG. 10A, a position on the cornea when the pupil center Puc is seen from the vertical direction (Z-direction) is P0. However, when the pupil center Puc is seen from the vertical direction in a state as shown in FIG. 10B where the eye is inclined, a corresponding point on the cornea becomes a position P1 deviated by Δd from the position P0. By a mechanism which performs tracking in the horizontal direction only with reference to the pupil center Puc without considering the eye inclination, laser irradiation cannot be performed with reference to the fixed position P0 on the cornea in a state where the eye is inclined, and thereby appropriate corneal ablation with high accuracy cannot be performed.

On the contrary, the apparatus of the present invention is capable of detecting the movement of the eye including the eye inclination to change a reference axis of the laser irradiation in accordance with the inclination angle α of the eye, which enables the laser irradiation with reference to the fixed position P0 on the cornea. Accordingly, the corneal ablation with high accuracy can be performed.

Here, if the patient's eye E moves fast and the speed exceeds a permissible range so that the tracking by movement of the parallel-link mechanism 100 cannot follow the eye, the control unit 130 outputs a stop signal for the laser irradiation to the main body 31 of the laser irradiation apparatus. Thereafter, if the irradiation end unit 30 which moves with the movement part 102 tracks to catch up with the eye movement and the mechanism 40 for eye detection detects that the eye movement is within the permissible range of the laser irradiation, the control unit 130 outputs a permissible signal for the laser irradiation to re-start the laser irradiation.

Incidentally, scanning mirrors of the galvano mirrors 34 and 36 can be operated much faster than the parallel-link mechanism 100. Therefore, if there is no eye inclination with respect to the optical axis L1 while there is a change in only a position on an orthogonal plane to the optical axis L1, the position of the laser irradiation by the galvano mirrors 34 and 36 can be moved so as to track the eye movement based on the detected information by the mechanism 40 for eye detection. In this case, the scanning control part 39 controls scanning operations of the galvano mirrors 34 and 36 in parallel with the movement of the irradiation end unit 30 and the microscope 20 by the parallel-link mechanism 100. Accordingly, the surgery can be performed smoothly without suspending the laser irradiation. When the mechanism 40 for eye detection detects that the eye inclination exceeds a permissible range, the laser irradiation is stopped as above.

For the irradiation optical system for corneal ablation arranged in the laser irradiation end unit 30, employed can be not only the optical system for scanning the beam with the small spot, but also an optical system for changing corneal curvature by a large beam using an aperture with a variable opening diameter. In addition, the parallel-link mechanism 100 having the six types of degrees of flexibility may include six control rods which are capable of expanding and contracting with complete control in stead of the control rods 111 to 116 which are capable of changing the bending angles. It is preferable only if the parallel-link mechanism 100 has at least the six control rods 111 to 116 capable of individually changing positions where the laser irradiation optical system and the microscope 20 are supported, and the driving sources which drives the control rods. A construction equivalent to the control rods which are capable of changing the bending angles or capable of expanding and contracting includes a mechanism for performing slide movement of the base parts of the control rods 111 to 116 on straight rails.

Figure 11:
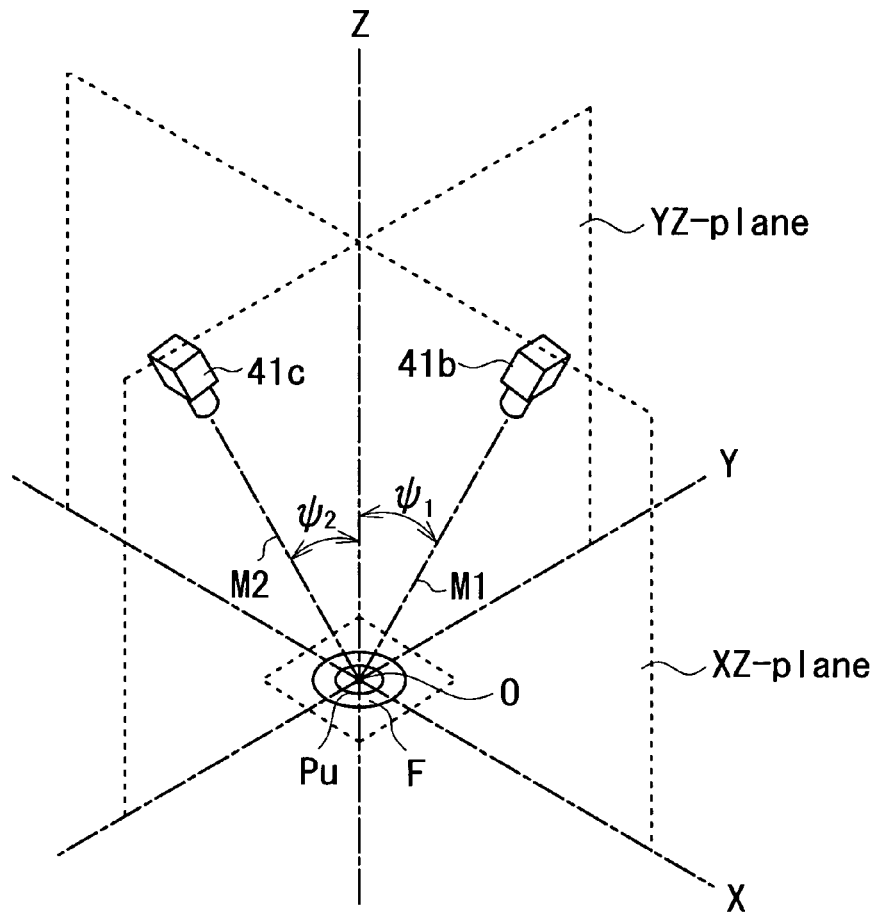
FIG. 11 is a view for illustrating another method of detecting the eye inclination.

A description will be given to an example of a method of detecting the eye inclination based on the anterior-segment images picked up by the cameras 41b and 41c included in the mechanism 40 for eye detection. In FIG. 11, assume that a direction of the optical axis L1 being the reference axis of the laser irradiation optical system and the microscope 20 is a Z-axis direction, and that an image-pickup optical axis M1 of the camera 41b and an image-pickup optical axis M2 of the camera 41c are placed respectively in the X-axis direction and the Y-axis direction orthogonal to the Z-axis direction (the optical axis L1) in a like manner shown in FIG. 5). In addition, assume that the image-pickup optical axis M1 of the camera 41b is placed to be inclined at an angle ψ1 in the X-axis direction with respect to the Z-axis direction, and the image-pickup optical axis M2 of the camera 41c is placed to be inclined at an angle ψ2 in the Y-axis direction. For example, assume that ψ1=ψ2=35°. In addition, the image-pickup optical axes M1 and M2 are arranged to intersect at a predetermined point O on the Z-axis. For the sake of simplicity of the description, an intended alignment state is set to be a case where an iris surface F is vertical to the Z-axis. In this case, assume that the pupil edge Pu and the iris surface F are circular seen from the Z-axis direction, and that the pupil center Puc coincides with the point O on the Z-axis. In addition, assume that the images picked up by the cameras 41b and 41c are projection images onto an image-pickup element surfaces with no optical distortion.

As for the detection of the eye inclination, there are a method of detection based on a distortion direction of the pupil shapes, and a method of detection based on size ratios of the pupil shapes in two directions. First, a description will be given to the method of detecting the eye inclination based on a distortion direction of the pupil shapes.

Figures 12A, 12B:
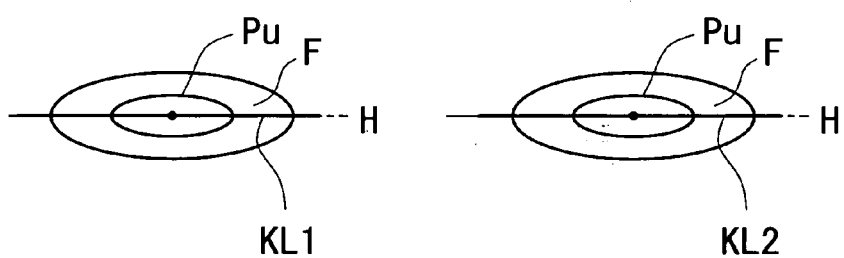
FIGS. 12A and 12B are views showing elliptical shapes of a pupil edge picked up by two cameras when the eye is in a horizontal state.

When the iris surface F is vertical to the Z-axis, the shapes of the pupil edges Pu images picked up by the cameras 41b and 41c are detected as elliptical shapes of which long axes are in horizontal states as shown in FIGS. 12A and 12B. In FIG. 12A, shown is a state where the pupil edge Pu and the iris surface F image picked up by the camera 41b in the X-axis direction are elliptical, and an ellipse's long axis KL1 of the pupil edge Pu is in a horizontal direction H. Similarly, in FIG. 12B, shown is a state where the pupil edge Pu image and the iris surface F image picked up by the camera 41c in the Y-axis direction are elliptical, and an ellipse's long axis KL2 of the pupil edge Pu is in the horizontal direction H. Besides, the elliptical shapes of the pupil edges Pu can be detected by subjecting the pupil edges Pu in the picked-up images to ellipse fitting processing (processing for fitting the pupil edge Pu to an ellipse by the least-squares method).

Figure 13A:
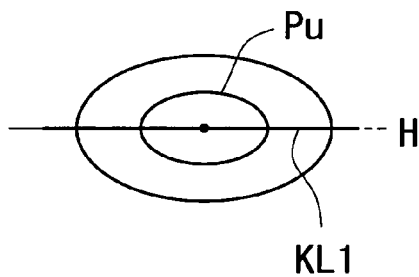
FIGS. 13A and 13B are views showing elliptical shapes of the pupil edge picked up by the two cameras when the eye is inclined only in an X-axis direction.
Figure 13B:
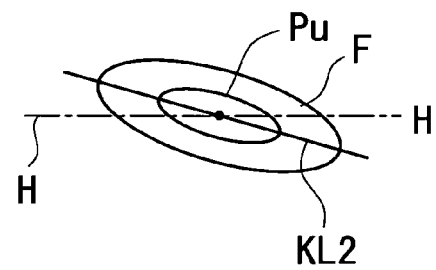

Next, a case where the iris surface F is inclined from the horizontal state (where the eye rotates) will be considered. In a case where the eye is inclined only in the X-axis direction, an eccentricity of the ellipse changes in the elliptical shape of the pupil edge Pu image picked up by the camera 41b in the X-axis direction and the long axis KL1 remains in the horizontal direction with no change (see FIG. 13A), while in the elliptical shape of the pupil edge Pu image picked up by the camera 41c in the Y-axis direction, the long axis KL2 is detected in a state where its direction is inclined to the right or the left with respect to the horizontal direction H (see FIG. 13B). In a case where the eye is inclined only in the Y-axis direction, the elliptical shape images picked up by the cameras 41b and 41c have relations respectively inverse to FIGS. 13A and 13B. Accordingly, in the detection method, information on the eye inclination in an X-axis direction component can be detected by the camera 41c in a Y-axis direction, and information on the eye inclination in the Y-axis direction component can be detected by the camera 41b in the X-axis direction.

Figure 14:
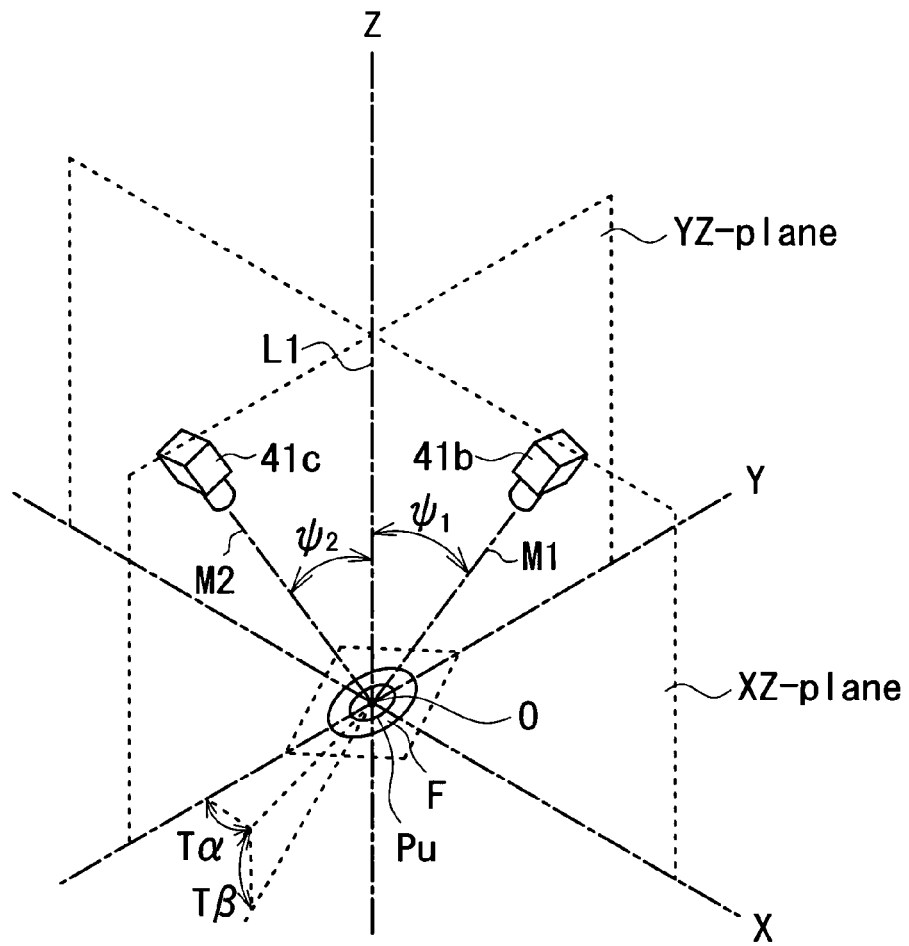
FIG. 14 is a view for illustrating a case where the eye is inclined in the X-axis direction and a Y-axis direction.
Figures 15A, 15B:
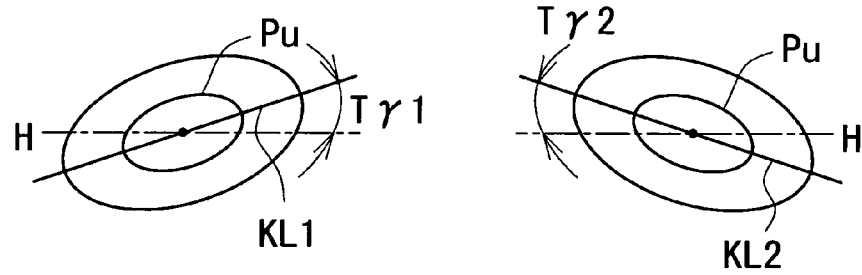
FIGS. 15A and 15B are views for illustrating inclination of elliptical shapes of the pupil edge picked up by the two cameras when the eye is inclined in the X-axis and Y-axis directions.

Further, a case where the eye is inclined in the X-axis direction and the Y-axis direction will be considered. As shown in FIG. 14, assume that the iris surface F is inclined in a direction of an angle Tα from the Y-axis on an XY-plane and at an angle Tβ with respect to the XY-plane, from the horizontal state. In this respect, as for the elliptical shape of the pupil edge Pu image picked up by the camera 41b in the X-axis direction, assume that an angle of the ellipse's long axis KL1 with respect to the horizontal direction H is Tγ1 (see FIG. 15A), and as for the elliptical shape of the pupil edge Pu picked up by the camera 41c in the Y-axis direction, assume that an angle of the ellipse's long axis KL2 with respect to the horizontal direction H is Tγ2 (see FIG. 15B), the following expressions hold.

tan Tγ1=tan Tβ×cos(90+Tα)/cos ω1×(tan ψ1−tan Tβ×sin(90+Tα))     (Expression 1)

tan Tγ2=tan Tβ×cos Tα/cos ψ2×(tan ψ2−tan Tβ×sin Tα)     (Expression 2)

In the above two expressions, the angles ψ1 and ψ2 are already known according to the design, Tγ1 and Tγ2 can be detected by subjecting the pupil edge Pu images picked up by the cameras 41b and 41c to image processing; therefore, the angles Tα and Tβ can be obtained. In the detection of the eye inclination, directions of the ellipse's minor axes can be used instead of the long axis directions.

Incidentally, in the method of detecting the elliptical shapes as mentioned above, when the eye is inclined at the angles (ψ1 and ψ2) formed between the Z-axis (the optical axis L1=the reference axis of the laser irradiation optical system) and respective the image-pickup optical axes of the cameras 41b and 41c, the shapes of the pupil edge Pu images becomes circular, and the long axis directions disappear. On the contrary, if angles formed between the iris surface F and the respective cameras 41b and 41c are 90° and more, the pupil cannot be detected. Eccentricities of the ellipses become higher as the angles ψ1 and ψ2 become larger, which facilitates the detection as an ellipse; however, when the angles are more than 45°, balances of detection ranges of the inclination becomes unfavorable. Further in this case, a nose, a cheek and the like are apt to be shadows in photographing. On the contrary, the eccentricities of the ellipses become lower as the angles ψ1 and ψ2 become smaller, which causes difficulty in the detection as an ellipse and also narrows the detection ranges. Accordingly, it is preferable that the angles ψ1 and ψ2 are 30° or more, and 45° or less.

In addition, an angle formed between the image-pickup optical axes of the cameras 41b and 41c is preferably in a range of 70° to 110°. When the angle formed between the image-pick up optical axes is made 90° (in an orthogonal relationship) as in the above preferred embodiment, the inclination of the elliptical shapes of the pupil edge images picked up in the different directions are easily detected, which is especially preferable.

Figure 16:
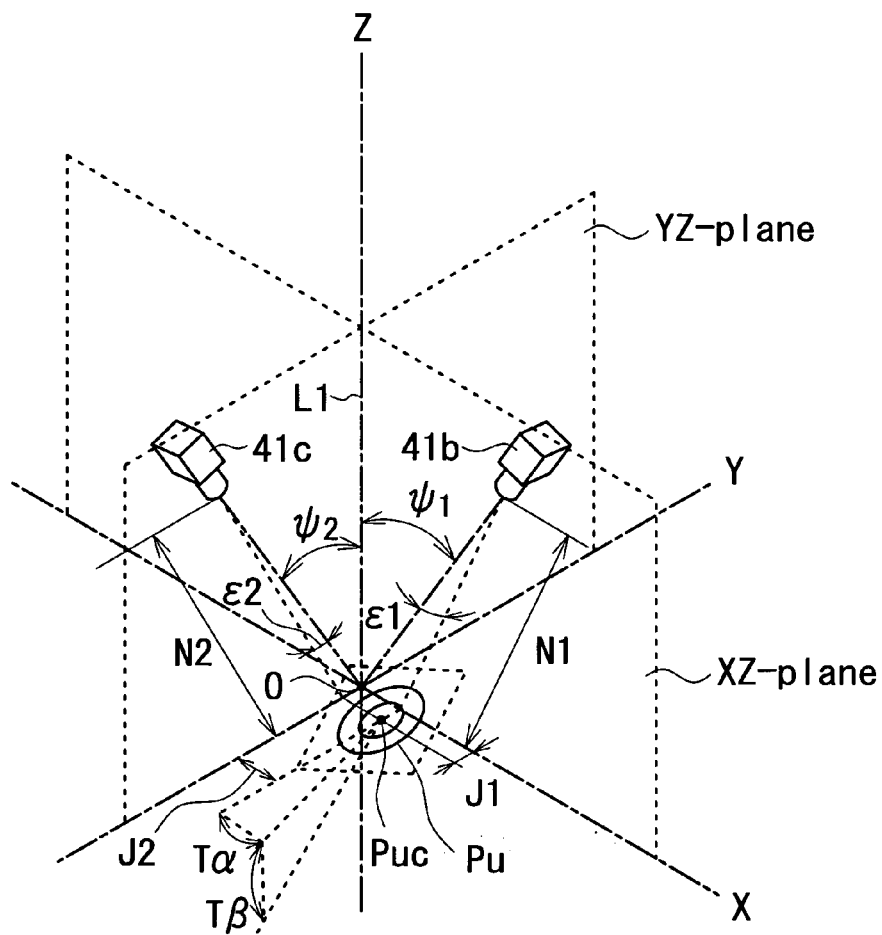
FIG. 16 is a view for illustrating a case where the eye shown in FIG. 14 has positional deviations in X- and Y-directions.

FIG. 16 is a view for illustrating a case where the eye shown in FIG. 14 has positional deviations in the X- and Y-directions. As for the positional deviations of the eye, assume that a change in an angle in a vertical direction seen from the camera 41*b* is $\epsilon 1$ (indicating the positional deviation in the vertical direction), that a distance in the vertical direction from the camera 41*b* to the pupil center Puc is N1, and that the positional deviation in a lateral direction is J1. In this respect, as for the elliptical shape of the pupil edge Pu image picked up by the camera 41*b*, assume that an angle of the ellipse's long axis KL1 with respect to the horizontal direction H is T$\rho$1 (see FIG. 17A), the following expression holds.

$$\tan T\rho1 = \tan^{-1}(J1/N1 \times \tan(\psi1-\epsilon1)) + \tan^{-1}(\tan T\beta \times \cos(90+T\alpha)/\cos(\psi1-\epsilon1) \times (\tan(\psi1-\epsilon1) - \tan T\beta \times \sin(90+T\alpha)))$$ (Expression 3)

J1 which is the positional deviation of the eye in the Y-direction can be detected from a deviation amount of the pupil center Puc from the image-pickup optical axis of the camera 42*b* in the lateral direction. $\epsilon 1$ and N1 can be calculated from arrangement conditions of the camera 41*b* if a deviation amount of the pupil center Puc from the image-pickup optical axis in the vertical direction is figured out.

In addition, assume that a change in an angle in the vertical direction seen from the camera 41*c* is $\epsilon 2$ (indicating the positional deviation in the vertical direction), that a distance in the vertical direction from the 41*c* to the pupil center Puc is N2, and that the positional deviation in the lateral direction is J2. In this respect, as for the elliptical shape of the pupil edge Pu image picked up by the camera 41*c*, assume that an angle of the ellipse's long axis KL2 with respect to the horizontal direction H is T$\rho$2 (see FIG. 17B), the following expression holds.

$$\tan T\rho2 = \tan^{-1}(J2/N2 \times \tan(\psi2-\epsilon2)) + \tan^{-1}(\tan T\beta \times \cos T\alpha/\cos(\psi2-\epsilon2) \times (\tan(\psi2-\epsilon2) - \tan T\beta \times \sin T\alpha)$$ (Expression 4)

J2 which is the positional deviation of the eye in the X-axis direction can be detected from a deviation amount of the pupil center Puc from the image-pickup optical axis of the camera 41*c* in the lateral direction. $\epsilon 2$ and N2 can be calculated from arrangement conditions of the camera 41*c* if the deviation amount of the pupil center Puc from the image-pickup optical axis in the vertical direction is figured out.

Incidentally, the positional deviation of the eye in the X-axis direction can be detected as K1 which is a deviation of the pupil center Puc in the vertical direction detected by the camera 41*b*, as shown in FIG. 17A. The positional deviation of the eye in the Y-axis direction can be detected as K2 which is a deviation of the pupil center Puc in the vertical direction detected by the camera 41*c*, as shown in FIG. 17B.

Here, a case where the eye has a further positional deviation of $\delta Z$ in the Z-axis direction will be considered. In this case, assume that a change from the positional deviation K1 of the eye in the X-axis direction detected by the camera 41*b* is K$\delta$Z1, the following expression holds.

$$K\delta Z1 = K1 + \delta Z \times \tan \psi1$$ (Expression 5)

Meanwhile, the positional deviation of the eye in the Y-axis direction detected by the camera 41*b* remains J1 with no change. Similarly, in a case where the eye has the positional deviation of $\delta Z$ in the Z-axis direction, assume that a change from the positional deviation K2 of the eye in the Y-axis direction detected by the camera 41*c* is K$\delta$Z2, the following expression holds.

$$K\delta Z2 = K2 + \delta Z \times \tan \psi2$$ (Expression 6)

Meanwhile, the positional deviation of the eye in the X-axis direction detected by the camera 41*c* remains J2 with no change. Accordingly, information on the positional deviations in the X- and Y-directions and information on the positional deviation in the Z-direction are obtained based on the detected information on the pupil positions by the two cameras 41*b* and 41*c*. Information on eye inclination when the eye has the positional deviation in the Z-direction may be calculated by offsetting the positional deviation in the Z-direction.

In the above-mentioned detection of the positional deviations and the inclination of the patient's eye with respect to the reference axis, the shapes of the pupil edge Pu images picked up from slanting directions are obtained by ellipse fitting, and the inclination information is calculated based on the long axes (or the minor axes) of the ellipses. This method has high accuracy while time is needed for calculation processing. Hence, a simplified method of detecting the information on the position and the inclination of the eye will be described with reference to FIG. 18.

In FIG. 18, shown is an image of the pupil edge Pu in the anterior-segment image picked up by the cameras 41*b* or 41*c*. In FIG. 18, assume that the center in the anterior-segment image is Co, a horizontal axis passing through the center Co is x, and a vertical axis passing through the center Co is y. A pupil portion in the anterior-segment image is scanned horizontally and vertically to detect positions of the pupil edge Pu on both the scanning lines. When a start point HSns and an end point HSne of the pupil edge Pu are detected on a horizontal scanning line HSn, a middle point HSnm between the start point HSns and the end point HSne is obtained. Similarly, when start points HSns and end points HSne of the pupil edge Pu are detected on the other horizontal scanning lines HSn, middle points HSnm therebetween are obtained. Then a regression line HRL is obtained with respect to the middle points HSnm on the horizontal scanning lines.

Also for the scanning in the vertical direction, when a start point VSns and an end point VSne of the pupil edge Pu on a vertical scanning line VSn are detected, a middle point VSnm between the start point VSns and the end point VSne is obtained. After detecting start points VSns and end points VSne of the pupil edge Pu on the other vertical scanning lines, middle points VSnm therebetween are obtained. Then, a regression line VRL is obtained with respect to the middle points VSnm on the vertical scanning lines.

The pupil center Puc can be obtained as an intersection point of the regression line HRL in the horizontal scanning and the regression line VRL in the vertical scanning. The information on the positional deviations of the eye can be obtained as positional deviations of the pupil center Puc in the X- and Y-directions with respect to the center Co of the picked-up image. The information on the eye inclination can be obtained as an inclination angle THR$\gamma$ of the regression line HRL with respect to the horizontal scanning direction (or, can be obtained as an inclination angle of the regression line VRL with respect to the vertical scanning direction). The inclination information is not as precise as the aforementioned inclination information; however, at least a degree of the eye inclination can be detected therefrom. According to this method, the processing for fitting the pupil edge Pu to the elliptical shape is not needed at the time of detecting the information on the eye inclination, which allows the time for the calculation processing to be reduced. Besides, the number of the scanning lines in the horizontal direction and the vertical direction may be increased or decreased in consideration of accuracy and the calculation time.

The position of the patient's eye may be detected to be obtained as a barycenter position in an area surrounded by the pupil edge Pu. The information on the eye inclination can be detected to be obtained also by another method of employing the anterior-segment images of the pupil or the iris obtained by the two cameras 41b and 41c, while the above-described method is one example.

Figure 19:
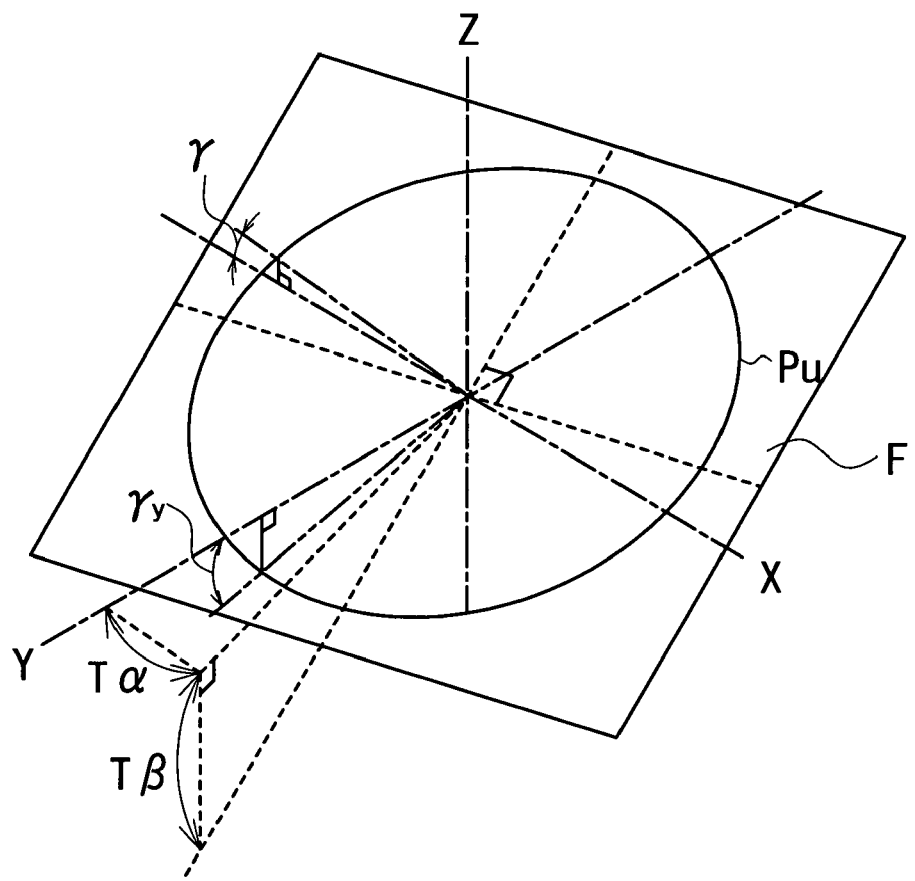
FIG. 19 is a view for illustrating a case where the pupil edge of the eye is inclined.

Next, a description will be given to the method of detecting the eye inclination based on size ratios of the pupil shapes in two directions with reference to the pupil centers of the pupil shapes. FIG. 19 is a view for illustrating a case where the pupil edge Pu on the iris surface F is inclined in the direction of the angle Tα from the Y-axis on the XY-plane and at the angle Tβ with respect to the XY-plane, similarly to FIG. 14. In FIG. 19, assume that an angle between the iris surface F and the X-axis when the iris surface F crosses the XZ-plane is γx, and that an angle between the iris surface F and the Y-axis when the iris surface F crosses the YZ-plane is γy. In this respect, the following mathematical relations hold among the inclination angles Tα, Tβ and the angles γx, γy.

$$\tan \gamma x = \cos(T\alpha + 90) \times \tan T\beta \quad \text{(Expression 7)}$$

$$\tan \gamma y = \cos T\alpha \times \tan T\beta \quad \text{(Expression 8)}$$

Figure 20:
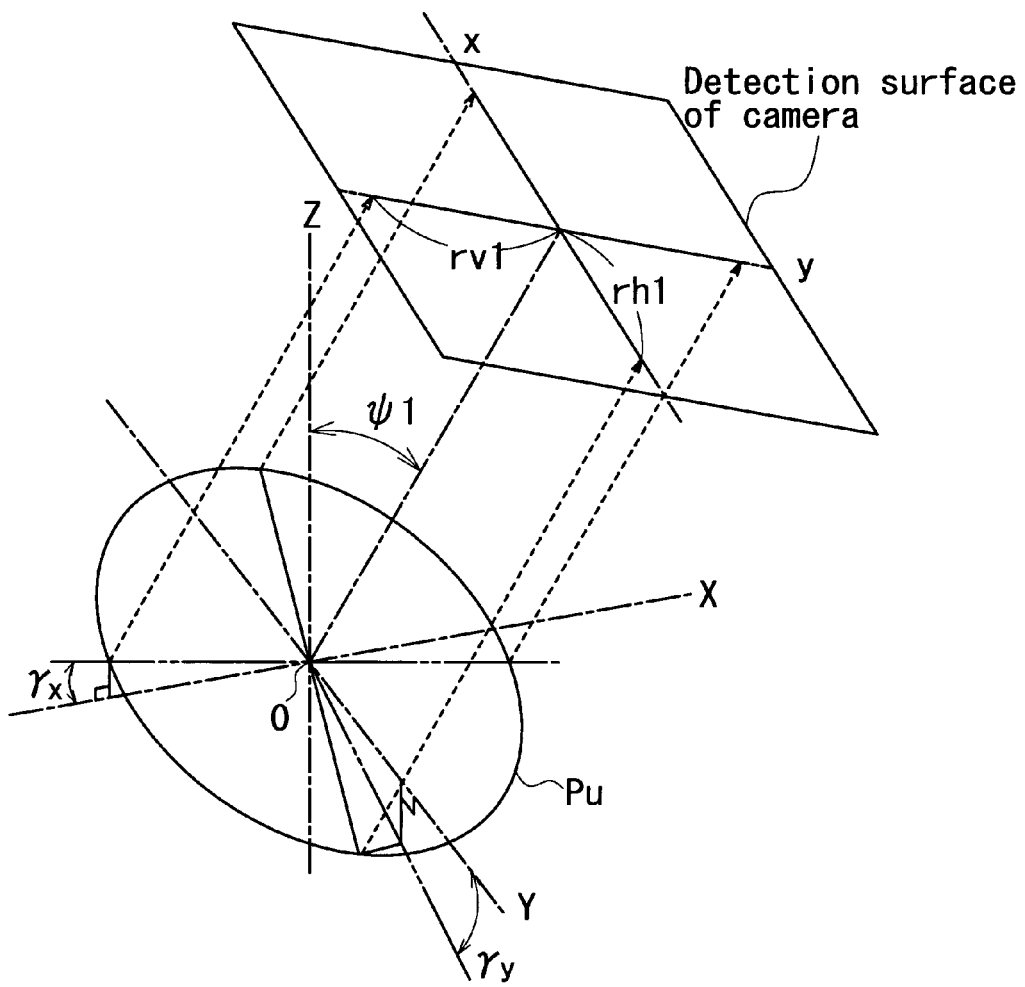
FIG. 20 is a view for illustrating a change in a pupil shape projected onto a detection surface of the X-axis camera.
Figures 21A, 21B:
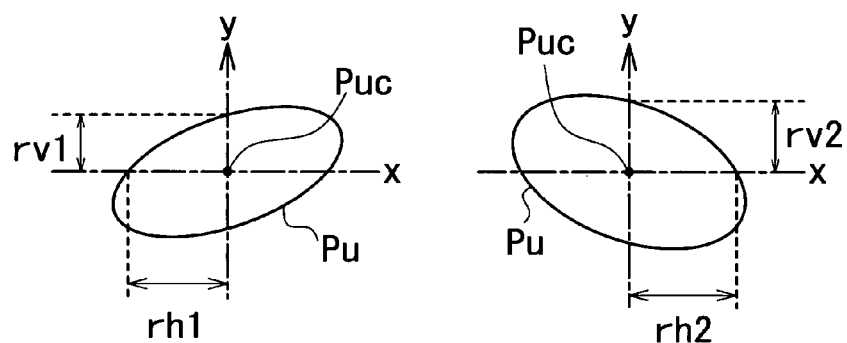
FIGS. 21A and 21B are views showing sizes of the pupil edges in a vertical direction and a horizontal direction projected onto detection surfaces of the X-axis camera and the Y-axis camera.

In addition, FIG. 20 is a view for illustrating change in the pupil shape projected onto a detection surface of the X-axis camera 41b with respect to the inclined pupil edge Pu (a viewing direction is changed with respect to FIG. 19). As for the pupil shape projected onto the detection surface of the camera 41b at this time, assume that sizes of the pupil edge Pu from the pupil center Puc in the vertical direction (the x-axis direction) and the horizontal direction (the y-axis direction) are rv1 and rh1 respectively as shown in FIG. 21A. Similarly, as for the pupil shape projected onto a detection surface of the Y-axis camera 41c, assume that sizes of the pupil edge Pu from the pupil center Puc in the vertical direction (the x-axis direction) and the horizontal direction (the y-axis direction) are rv2 and rh2 respectively as shown in FIG. 21B. Assume that the pupil edge Pu has a radius; the radius=r, the sizes rv1 and rv2 in the vertical direction can be expressed as follows.

$$rv1 = r \times \cos(\psi 1 - \gamma x) \quad \text{(Expression 9)}$$

$$rv2 = r \times \cos(\psi 2 - \gamma y) \quad \text{(Expression 10)}$$

Figure 22:
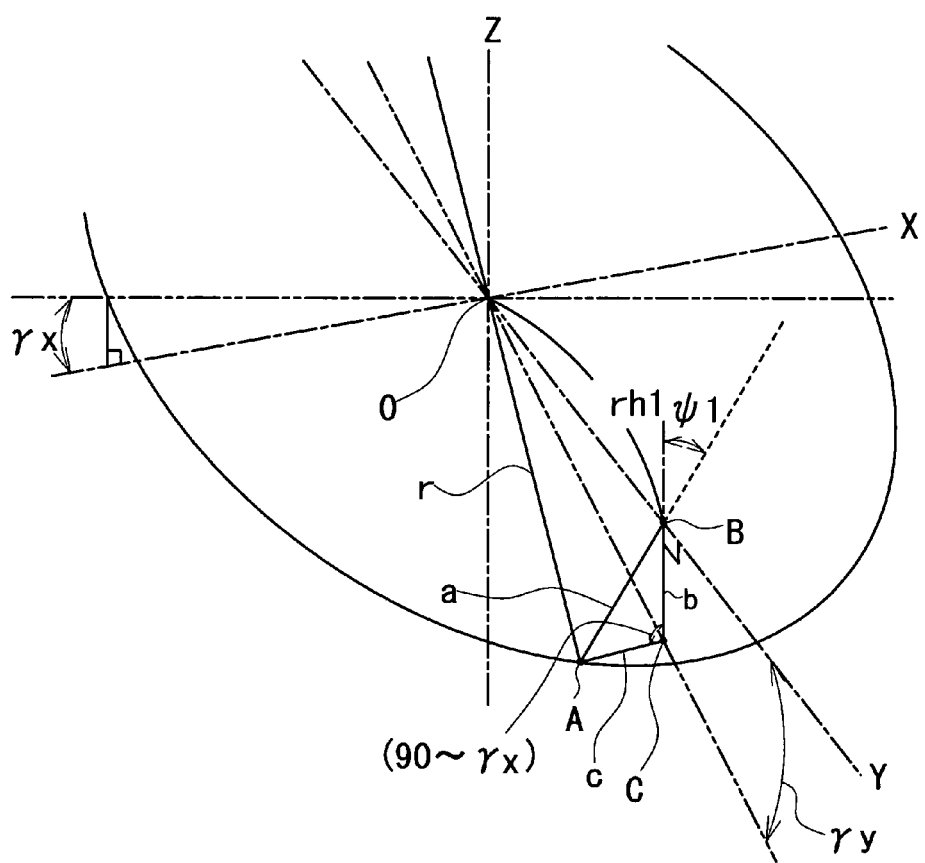
FIG. 22 is an enlarged view showing a part of FIG. 20.

Next, the size rh1 in the horizontal direction projected onto the detection surface of the camera 41b will be described with reference to FIG. 22. FIG. 22 is an enlarged view showing a part of FIG. 20. In FIG. 22, assume that the pupil edge originated from the pupil center of the camera 41b projected onto the Y-axis is a point A, that an intersection point of a line extending from the point A in a projection direction of the camera 41b (a direction of the angle ψ1) and the Y-axis is a point B, and that an intersection point where a line extending in the Z-direction from the point B intersects with the iris surface F inclined at the angle γy is a point C. Assume that a measure of a line segment AB is a, a measure of a line segment BC is b, and a measure of a line segment CA is c. As shown in FIG. 22, a line segment OB=rh1, and a line segment OA=r, so that the following expressions hold.

$$r^2 = a^2 + rh1^2 \quad \text{(Expression 11)}$$

$$b = rh1 \times \tan \gamma y \quad \text{(Expression 12)}$$

In addition, in considering a triangle ABC, the line segment BC and the line segment AC forms an angle; the angle=(90−γx), and the line segment AB and the line segment AC forms an angle; the angle={180−ψ1−(90−γx)}, so that, by a sine theorem, there is a relation; a/sin(90−γx)=b/sin {180−ψ1−(90−γx)}. Accordingly, the measure of the line segment AB can be calculated mathematically as follows.

$$a = b \times \sin(90 - \gamma y)/\sin(\psi 1 + 90 - \gamma x) \quad \text{(Expression 13)}$$

Based on the above Expressions 11, 12 and 13, rh1 is obtained by the following expression.

$$rh1 = \frac{r}{\sqrt{1 + \left\{\frac{\tan \gamma y \times \sin(90 - \gamma x)}{\sin(\varphi 1 + 90 - \gamma x)}\right\}^2}} \quad \text{(Expression 14)}$$

Similarly, rh2 is calculated as follows.

$$rh2 = \frac{r}{\sqrt{1 + \left\{\frac{\tan \gamma y \times \sin(90 - \gamma y)}{\sin(\varphi 2 + 90 - \gamma y)}\right\}^2}} \quad \text{(Expression 15)}$$

Based on the above Expressions 9 and 14, a size ratio Q1=rv1/rh1 between the vertical size and the horizontal size of the pupil edge Pu obtained by the camera 41b is calculated by the following expression from which the radius r of the pupil edge Pu is eliminated.

$$Q1 = \cos(\varphi 1 - \gamma x) \times \sqrt{1 + \left\{\frac{\tan \gamma y \times \sin(90 - \gamma x)}{\sin(\varphi 1 + 90 - \gamma x)}\right\}^2} \quad \text{(Expression 16)}$$

Similarly, a size ratio Q2=rv2/rh2 between the vertical size and the horizontal size of the pupil edge Pu obtained the camera 41c is calculated by the following expression from which the radius r of the pupil edge Pu is eliminated.

$$Q2 = \cos(\varphi 2 - \gamma y) \times \sqrt{1 + \left\{\frac{\tan \gamma x \times \sin(90 - \gamma y)}{\sin(\varphi 2 + 90 - \gamma y)}\right\}^2} \quad \text{(Expression 17)}$$

In the above Expressions 16 and 17, Q1 and Q2 can be calculated by subjecting the respective anterior-segment images obtained by the cameras 41b and 41c to image processing to detect the pupil edge Pu. The angles ψ1 and ψ2 are already known according to the design. Accordingly, γx and γy are calculated by the two Expressions 16 and 17. If γx and γy are figured out, the inclination angles Tα and Tβ indicating the eye inclination are calculated by substituting γx and γy into the above-mentioned Expressions 7 and 8.

In addition, if the pupil center Puc of the eye deviates by J2 in the X-axis direction and by J1 in the Y-axis direction as shown in FIG. 16, the pupil center Puc can be calculated by subjecting the pupil centers Puc obtained by the cameras 41b and 41c to the image processing. Then, by calculating Q1 by the Expression 15 and Q2 by the Expression 16 with reference to the pupil center Puc, the angles Tα and Tβ in this respect are calculated. Further, also in a case where the eye has the positional deviation of δZ in the Z-axis direction, the positional deviation can be calculated by the above-mentioned Expressions 5 and 6. Accordingly, the three-dimensional positional deviation of the eye can be calculated based on the anterior-segment images obtained by the two cameras 41b and 41c.

Incidentally, in the method of detecting the eye inclination based on the size ratios in the pupil shapes in the two directions by the two cameras 41b and 41c, the vertical sizes and the horizontal sizes used in obtaining the size ratios of the pupil edges are mere examples, which are used because the X-axis and the Y-axis intersecting at right angles on the images facilitate the detection processing; therefore, it is preferable to obtain size ratios in at least two directions. More preferably, size ratios in three directions or more are averaged, and thereby the pupil edge Pu can be processed approximately also in a case where the pupil edge Pu is not circular.

In addition, in the method of detecting the eye inclination based on the size ratios of the pupil shapes in the two directions, it is enough that the respective image-pickup optical axes of the cameras 41b and 41c are arranged in different directions and in predetermined relationships with the optical axis L1, and for example, one of the image-pickup optical axes may be coaxial with the optical axis L. In addition, in the detection of the eye inclination, the method of detection based on the distortion directions of the pupil shapes and the method of detection based on the size ratios of the pupil shapes in the two directions can be employed in combination.

If the information on the positional deviations and the inclination of the eye (Tα and Tβ) can be detected as mentioned above, the control unit 130 drives and controls the parallel-link mechanism 100 based on the detected information. For example, when the automatic alignment is actuated with the switch 146, the control unit 130 drives and controls the parallel-link mechanism 100 based on the information on the positional deviations and the inclination of the eye to move the microscope 20 and the laser irradiation optical system so that the optical axis L1 being the reference axis coincides with the pupil center (within a predetermined permissible range) and the optical axis L1 becomes vertical to the iris surface F (within a predetermined permissible range). If the positional deviation of the eye in the Z-direction is detected, the control unit 130 controls to move the microscope 20 and the laser irradiation optical system so that the positional deviation in the Z-direction falls within a permissible range.

In addition, after positioning the microscope 20 and the laser irradiation optical system in a predetermined reference state, if a signal for starting the automatic tracking is inputted with the switch 147, the control unit 130 stores information on a position and inclination of the eye with respect to the optical axis L1 which are detected in the reference state in a memory included in the control unit 130. As compared to the position and the inclination of the eye stored in the memory, if changes are detected in the position and the inclination of the eye at the time of the laser irradiation, the control unit 130 drives and controls the parallel-link mechanism 100 to move the microscope 20 and the laser irradiation optical system so that the position and the inclination of the eye are brought to the reference state. Also in a case where the positional deviation in the optical axis L1 direction (Z-direction) is detected, the control unit 130 controls to move the microscope 20 and the laser irradiation optical system so as to bring to the reference state. Accordingly, the laser beam can be irradiated onto a proper position on the cornea in accordance with the movement of the patient's eye including the eye inclination.

Incidentally, if the eye inclination is large at the time of the laser irradiation, there may be a case where the laser irradiation optical system and the microscope are moved largely. If the eye inclination is detected beyond the permissible range, the control unit 130 outputs a stop signal for the laser irradiation to the main body 31 of the laser irradiation apparatus to suspend the laser irradiation. By actuating the automatic alignment again, the operator can move the laser irradiation optical system and the microscope 20 to an alignment state at the time of starting the laser irradiation.

In addition, on a display device 160 connected to the control unit 160, the information on the inclination and the positional deviations of the eye is displayed. By checking a display on the display device 160 and operating the lever 141 and the switches arranged in the operation panel 140, the operator can perform alignment so that the microscope 20 and the laser irradiation optical system have an intended positional relationship with the patient's eye. Alternatively, by moving the patient's face while checking the information on the eye inclination displayed on the display device 160, the microscope 20 and the laser irradiation optical system can have the intended positional relationship with the patient's eye. Then, if the eye inclination is detected beyond the permissible range at the time of the laser irradiation, the laser irradiation is stopped by the control unit 130, so that it is essential only if the operator sets the patient's face straight while checking the information on the eye inclination displayed again on the display device 160. The information on the inclination and the positional deviations of the eye is based on the alignment state where the iris surface F is vertical to the optical axis L1.

The invention claimed is:

1. An ophthalmic apparatus having a laser irradiation optical system for irradiating a laser beam for corneal surgery onto a patient's eye, which performs alignment of a reference axis of the laser irradiation optical system so that the reference axis has a predetermined positional relationship with the patient's eye to perform irradiation of the laser beam, the apparatus comprising:
movement means for changing inclination and a position of the laser irradiation optical system with respect to the patient's eye;
first image-pickup means and second image-pickup means for picking up images of an anterior segment of the patient's eye, which have image-pickup optical axes arranged in different directions and arranged to have respective predetermined positional relationships with the reference axis;
detection means for detecting inclination and a position of the patient's eye with respect to the reference axis by subjecting the anterior-segment images picked up by the first and second image-pickup means to image processing; and
control means for controlling the movement means so that the reference axis is brought to an intended alignment state with respect to the patient's eye based on a result of detection by the detection means.

2. The ophthalmic apparatus according to claim 1, wherein the detection means obtains pupil shapes by subjecting the anterior-segment images picked up by the first and second image-pickup means to the image processing, and detects the inclination of the patient's eye based on distortion of the obtained pupil shapes with respect to pupil shapes in the intended alignment state.

3. The ophthalmic apparatus according to claim 2, wherein the detection means detects the inclination of the patient's eye based on size ratios of the pupil shapes in at least two directions with reference to pupil centers of the pupil shapes.

4. The ophthalmic apparatus according to claim 2, wherein the image-pickup optical axes of the first and second image-pickup means are arranged inclined in different directions with respect to the reference axis, and the detection means detects the inclination of the patient's eye based on distortion directions of the obtained pupil shapes.

5. The ophthalmic apparatus according to claim 4, wherein as for the obtained pupil shapes, the detection means obtains the distortion directions based on middle positions of pupil edges, which are obtained by scanning the obtained pupil shapes horizontally and vertically respectively on a plurality of lines.

6. The ophthalmic apparatus according to claim 1, wherein the control means controls the movement means based on changes in inclination and a position of the patient's eye obtained by the detection means at the time of the irradiation with respect to inclination and a position of the patient's eye obtained by the detection means in the intended alignment state.

7. The ophthalmic apparatus according to claim 1, wherein the movement means has a parallel-link mechanism comprising:
- at least six control rods which support the laser irradiation optical system while supporting positions thereof can be changed individually; and
- driving sources which drive the control rods respectively.

8. An ophthalmic apparatus having a laser irradiation optical system for irradiating a laser beam for corneal surgery onto a patient's eye, which performs alignment of a reference axis of the laser irradiation optical system so that the reference axis has a predetermined positional relationship with the patient's eye to perform irradiation of the laser beam, the apparatus comprising:
- movement means for changing inclination and a position of the laser irradiation optical system with respect to the patient's eye;
- first image-pickup means and second image-pickup means for picking up images of an anterior segment of the patient's eye, which have image-pickup optical axes arranged in different directions and arranged to have respective predetermined positional relationships with the reference axis;
- detection means for detecting inclination and a position of the patient's eye with respect to the reference axis by subjecting the anterior-segment images picked up by the first and second image-pickup means to image processing; and
- display means for displaying information on the inclination and the position of the patient's eye detected by the detection means.

9. An ophthalmic apparatus comprising:
- a microscope for observing a patient's eye;
- a parallel-link mechanism which changes inclination and a position of the microscope including:
  - at least six control rods which support a movement part in which the microscope is installed; and
  - driving sources, which drive the control rods respectively;
- input means for inputting signals for changing the inclination and the position of the microscope; and
- control means for controlling an operation of the parallel-link mechanism based on the input signals,
- wherein when the signals for changing the inclination is inputted by the input means, the control means controls the operation of the parallel-link mechanism to incline the microscope taking a predetermined position on an optical axis of an objective lens included in the microscope as a reference position, and controls the operation of the parallel-link mechanism to keep a distance between the reference position and the objective lens.

10. The ophthalmic apparatus according to claim 9, further comprising detection means having image-pickup means installed in the movement part in order to pick up an image of the patient's eye, for detecting an alignment state including inclination of the eye by subjecting the eye image picked up by the image-pickup means to image processing,
- wherein the control means controls the operation of the parallel-link mechanism so that the microscope has a predetermined positional relationship with the patient's eye based on a result of detection by the detection means.

11. The ophthalmic apparatus according to claim 10, wherein the control means controls the operation of the parallel-link mechanism so that the inclination and the position of the microscope track movement of the patient's eye based on the detection result by the detection means.

12. The ophthalmic apparatus according to claim 9, further comprising:
- first image-pickup means and second image-pickup means for picking up images of an anterior segment of the patient's eye, which have image-pickup optical axes arranged in different directions and arranged to have respective predetermined positional relationships with a reference axis of the microscope; and
- detection means for detecting inclination and a position of the patient's eye with respect to the reference axis by subjecting the anterior segment images picked up by the first and second image-pickup means to image processing,
- wherein the control means controls the operation of the parallel-link mechanism so that the microscope is brought to an intended alignment state with respect to the patient's eye based on a result of detection by the detection means.

* * * * *